(12) United States Patent
Feary et al.

(10) Patent No.: US 10,669,541 B2
(45) Date of Patent: Jun. 2, 2020

(54) MEANS AND METHODS FOR THE GENERATION OF MAMMALIAN PRODUCER CELLS FOR THE PRODUCTION OF RECOMBINANT PROTEINS

(71) Applicant: LONZA BIOLOGICS PLC, Slough (GB)

(72) Inventors: Marc Feary, Newmarket (GB); James Rance, Thame (GB); Robert Young, London (GB); Elizabeth C. Sayer, Redhill (GB); Christopher M. Smales, Chartham (GB)

(73) Assignee: LONZA BIOLOGICS PLC., Slough (GB)

( * ) Notice: Subject to any disclaimer, the term of this patent is extended or adjusted under 35 U.S.C. 154(b) by 0 days.

(21) Appl. No.: 14/910,267

(22) PCT Filed: Jul. 30, 2014

(86) PCT No.: PCT/EP2014/066352
§ 371 (c)(1),
(2) Date: Feb. 5, 2016

(87) PCT Pub. No.: WO2015/018703
PCT Pub. Date: Feb. 12, 2015

(65) Prior Publication Data
US 2016/0177300 A1    Jun. 23, 2016

(30) Foreign Application Priority Data

Aug. 6, 2013 (EP) .................................. 13179342

(51) Int. Cl.
*C12N 15/113* (2010.01)
*C12P 21/00* (2006.01)
*C12N 15/11* (2006.01)
*C07K 16/00* (2006.01)

(52) U.S. Cl.
CPC ............ *C12N 15/113* (2013.01); *C07K 16/00* (2013.01); *C12N 15/111* (2013.01); *C12P 21/00* (2013.01); *C12N 2310/141* (2013.01); *C12N 2330/51* (2013.01)

(58) Field of Classification Search
None
See application file for complete search history.

(56) References Cited

U.S. PATENT DOCUMENTS

| 8,476,244 B2 | 7/2013 | Gammell et al. |
| 8,951,983 B2 | 2/2015 | Hornstein et al. |
| 2010/0190258 A1 | 7/2010 | Gammell et al. |
| 2013/0209440 A1 | 8/2013 | Hornstein et al. |

FOREIGN PATENT DOCUMENTS

| WO | WO-2008/015662 A1 | 2/2008 | |
| WO | WO-2012/052872 A2 | 4/2012 | |
| WO | WO 2012052872 A2 * | 4/2012 | ........... C12N 5/0676 |

OTHER PUBLICATIONS

Calin et al., PNAS, 2008, vol. 105, pp. 5166-5171.*
Chang et al., Molecular Cell, 2007, vol. 26, pp. 745-752.*
Cimminio et al., PNAS, 2005, vol. 102, pp. 13944-13949.*
Chu et al., Current Trends in Biotechnology, 2001, vol. 12, pp. 180-187.*
He et al., Nat Rev Cancer, 2007, vol. 7(11) pp. 819-822.*
Kim et al., Appl Microbiol Biotechnol, 2011, vol. 93, pp. 917-930.*
Barron et al., Journal of Biotechnology, 2011, vol. 151, pp. 204-211.*
Linsley et al., Molecular and Cellular Biology, 2007, vol. 27(6) pp. 2240-2252.*
International Search Report and Written Opinion of the ISA for PCT/EP2014/066352; ISA/EP, Rijswijk, NL, dated Oct. 20, 2014.
International Preliminary Report on Patentability with annexes, IPEA/EP, Rijswijk, NL, dated Sep. 22, 2015.
Japanese Office Action in parallel application JP 2016-532318, JPO, dated Jun. 5, 2018.
Qing Ji et al., "Restoration of Tumor Suppressor miR-34 inhibits human p53-mutant gastric cancer tumorspheres", BMC Cancer 2008, 8:266, pp. 1-12.
Vaibhav Jadhav et al., "CHO microRNA engineering is growing up: Recent successes and future challenges", Biotechnology Advances 31 (2013) Aug. 2013, pp. 1501-1513.
Patrick Gammell, "MicroRNAs: recently discovered key regulators of proliferation and apoptosis in animal cells; Identification of miRNBAs regulating growth", Cytotechnology, vol. 53, No. 1-3, Feb. 20, 2007 (Feb. 20, 2007), pp. 55-63, XP019499818, ISSN: 1573-0778, DOI: 10.1007/s10616-007-9049-4.
Johnson, K. et al.: "Conserved MicroRNAs in Chinese hamster ovary cell lines,", Biotechnology and Bioengineering, vol. 108, No. 2, Feb. 11, 2011 (Feb. 11, 2011), pp. 475-480, XP055094801, ISSN: 0006-3592, DOI: 10.1002/bit.22940.

* cited by examiner

*Primary Examiner* — Mindy G Brown
(74) *Attorney, Agent, or Firm* — Lucas & Mercanti, LLP

(57) ABSTRACT

Methods for generating mammalian cells characterized by an increased concentration of at least one of miR-15, miR-16, and miR-34 for producing proteins at an industrial scale are provided. Methods for using the mammalian cells, in particular for the production of proteins of interest, are also provided.

14 Claims, 12 Drawing Sheets

Figure 1:
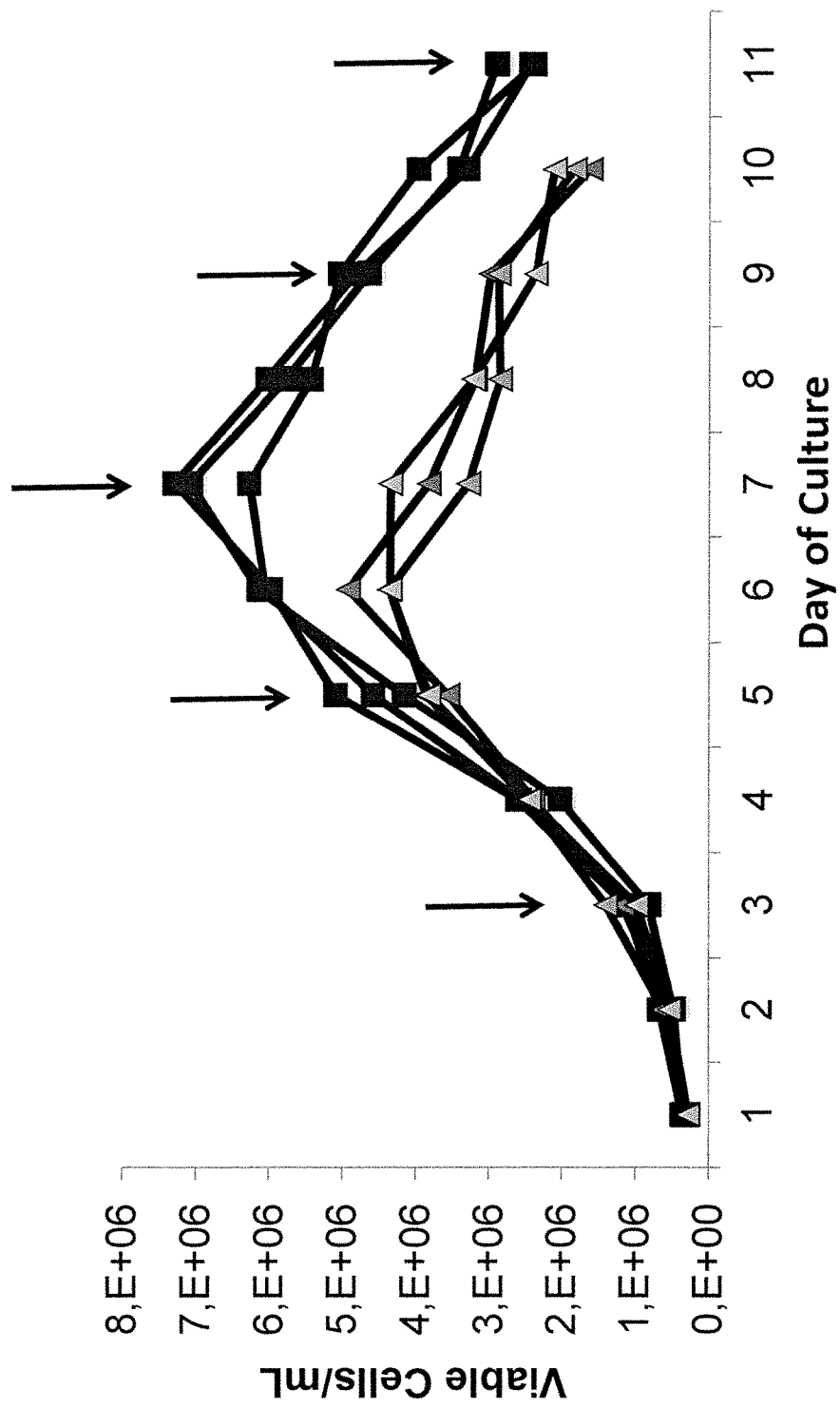

Specification includes a Sequence Listing.

SEQUENCE LISTING

```
<160> NUMBER OF SEQ ID NOS: 12

<210> SEQ ID NO 1
<211> LENGTH: 23
<212> TYPE: DNA
<213> ORGANISM: human

<400> SEQUENCE: 1
agtactgtag cagcacatca tgg                                           23

<210> SEQ ID NO 2
<211> LENGTH: 24
<212> TYPE: DNA
<213> ORGANISM: human

<400> SEQUENCE: 2
tttccttaaa tttctagagc agca                                          24

<210> SEQ ID NO 3
<211> LENGTH: 19
<212> TYPE: DNA
<213> ORGANISM: human

<400> SEQUENCE: 3
agcagtgcct tagcagcac                                                19

<210> SEQ ID NO 4
<211> LENGTH: 21
<212> TYPE: DNA
<213> ORGANISM: human

<400> SEQUENCE: 4
caaccttact tcagcagcac a                                             21

<210> SEQ ID NO 5
<211> LENGTH: 22
<212> TYPE: DNA
<213> ORGANISM: human

<400> SEQUENCE: 5
```

-continued ttccactcta gcagcacgta aa                                      22

<210> SEQ ID NO 6
<211> LENGTH: 23
<212> TYPE: DNA
<213> ORGANISM: human

<400> SEQUENCE: 6
gtcacactaa agcagcacaa taa                                     23

<210> SEQ ID NO 7
<211> LENGTH: 20
<212> TYPE: DNA
<213> ORGANISM: human

<400> SEQUENCE: 7
gtaccacctt gtcgggtagc                                         20

<210> SEQ ID NO 8
<211> LENGTH: 21
<212> TYPE: DNA
<213> ORGANISM: human

<400> SEQUENCE: 8
caaaatgtca gacagcccat c                                       21

<210> SEQ ID NO 9
<211> LENGTH: 23
<212> TYPE: DNA
<213> ORGANISM: human

<400> SEQUENCE: 9
ggcagtgtag ttagctgatt gct                                     23

<210> SEQ ID NO 10
<211> LENGTH: 21
<212> TYPE: DNA
<213> ORGANISM: human

<400> SEQUENCE: 10
tctttttacc tggctgtgtg g                                       21

<210> SEQ ID NO 11
<211> LENGTH: 21
<212> TYPE: DNA
<213> ORGANISM: human

<400> SEQUENCE: 11
agctgagagg gaaattgtgc g                                       21

<210> SEQ ID NO 12
<211> LENGTH: 18
<212> TYPE: DNA
<213> ORGANISM: human

<400> SEQUENCE: 12
gcaacggaac cgctcatt                                           18

MEANS AND METHODS FOR THE GENERATION OF MAMMALIAN PRODUCER CELLS FOR THE PRODUCTION OF RECOMBINANT PROTEINS

CROSS-REFERENCE TO RELATED APPLICATIONS

This application is a 371 U.S. National Stage of International Application No. PCT/EP2014/066352, filed on Jul. 30, 2014, which claims the benefit of and priority to European Patent Application EP 13179342.4, filed on Aug. 6, 2013. The entire disclosures of the above applications are incorporated herein by reference.

The present invention relates to the generation of mammalian cells capable of producing proteins at an industrial scale and means and methods to obtain and use said cells, in particular for protein production.

The generation and synthesis of recombinant proteins for various applications and processes is well-known to the skilled person. A wide variety of different means and methods are used employing various mechanisms to provide for a safe and efficient large-scale manufacture of said proteins. These cellular mechanisms may exert their effects at different stages of the protein production process, for instance at the transcriptional, translational or post-translational level. A relatively recently discovered mechanism by which translation, and hence gene expression, is controlled is via the expression of miRNAs (short for microRNAs, in the following also termed miRs). These are endogenous single-stranded non-coding RNA of approximately 22 nucleotides (nt) in length that generally act as negative regulators of gene expression by RNA:RNA interactions between the miR and the 3'-UTR of target mRNAs. miRs have been shown to play important regulatory roles in mRNA translation, and are involved in the control of cell development, differentiation, apoptosis, antiviral defences and most fundamental cellular processes. Indeed, it has been suggested that miRs might regulate expression of around 30% of the human genome. miRs influence and regulate mRNA translation rates by interacting with specific target cellular mRNAs, mainly at the 3'-UTR. Further, one miR may target and interact with multiple target mRNAs and therefore determining miR recognition motifs and targets is currently difficult.

To date the majority of studies investigating miR expression and the subsequent control these elicit on gene expression have been undertaken in the oncology field, although much of this knowledge is relevant to the industrial biotechnology field with respect to how these underpin cell phenotype. For example, studies in the cancer field that demonstrate the relationship between cell growth and miRs may be applicable in the biotechnology field. The wide range of potential targets that miRs can regulate offers the potential to develop cell lines with new phenotypes by manipulating gene expression via miR engineering. In doing this, it is realised that manipulation of a single miR could potentially target the regulation of multiple genes that together play a role in determining cell phenotype.

Part of the pathway for the biogenesis of miRs is shared with that of silencing or short interfering RNA (sRNA), involving Dicer and RNA-induced silencing complex (RISC) (Bartel et al. 2004 Cell 116:281-297). 70% of miR genes are reported to be found within introns or exons of genes, with the remaining 30% located within intergenic regions. Initially, the primary miR (pri-miR) is cleaved by RNase II endonuclease Drosha and Pasha forming a stem-loop structure called a pre-miRNA (pre-miR). This pre-miR is around 60 to 70 nucleotides in length, and has a 5' phosphate and a 2 nucleotide over hang on the 3' end. Along with the transport cofactor Ran-GTP the pre-miR hairpin is actively transported from the nucleus through the receptor Exportin-5. In the cytoplasm an RNase III endonuclease called Dicer is thought to interact with the pre-miR by recognising the double stranded portion, and cutting approximately two helical turns away from the base of the stem-loop, leaving a miR:miR* duplex (the opposing arm of the pre-miR is denoted by an asterisk after the miR name). This miR:miR* duplex enters RISC, and the miR* component of the miR:miR* duplex is peeled away and degraded via the aid of a helicase. The 5' end of the mature miR lies at the end of a strand of the miR-miR* duplex with the lowest thermodynamic energy (Bartel et al. 2004 Cell 116: 281-297).

The first one to seven nucleotides at the 5' end of the miR bind to the target via base-pairing and is termed the 'seed' region. In mammalian cells miRs usually recognise target genes via imperfect base pairing to the mRNA where only the seed region of the miR exhibits a perfect match to the target. It has also been reported that miR binding sites exist in other locations other than the 3' end of mRNA, such as the 5'-untranslated region (UTR) of ribosomal protein mRNA (Ørom et al. 2008 Molecular Cell 30:460-471), or even genomic regulatory sequences such as promoters (e.g., Tan et al. 2009 BMC Molecular Biology 10:12). There are also reports that miRs can interact with mRNAs in the coding sequence (Rigoutsos et al. 2009 Cancer Research 69:3245-3248). However, less information on the non 3'-UTR interactions exist and most validated miR targets are located in mRNA 3'-untranslated regions (3'UTRs). Generally, if there is incomplete base-pairing between the miR and mRNA target, translational inhibition occurs, whereas it is thought that where there is complete base-pairing target mRNA degradation occurs.

Despite the potential use of miRs to regulate gene expression and hence pathways and cellular processes that influence high recombinant protein productivity, to date the manipulation of miRs to improve the production of recombinant proteins from cultured mammalian cells has not been fully realised. The concentration of secreted recombinant protein in culture medium is a function of cell-specific production rate (qP) and the time integral of viable cell concentration (IVC) (Porter et al. 2010 Biotechnology Progress 26:1446-1455). Hence, miRs could be applied to pathways to increase qP (e.g., through manipulation of secretory pathways) or IVC (e.g., through manipulation of proliferative or apoptotic pathways). The majority of studies into miR expression and manipulation in the bioprocessing/biotechnology field have centred on different Chinese hamster ovary (CHO) cell lineages. However, one study that profiled miRs in human embryonic kidney 293 (HEK293) cells (often used for transient production of recombinant protein), followed how the miR expression profile changed during different growth-phases in batch culture (Koh et al. 2009 Journal of Biotechnology 140:149-155). These authors reported that 14 miRs changed significantly in expression between exponential and stationary growth phases, 13 being up-regulated in stationary phase. Amongst those miRs observed to change between exponential and stationary phase were miR-15a and miR-16 (Koh et al. 2009 Journal of Biotechnology 140:149-155).

Recently, CHO cell miR expression and the manipulation of miRs in CHO cells have attracted much interest, although such studies are still in their infancy. A recent study used deep sequencing approaches to profile conserved miRs and their expression across recombinant cell lines (Hammond et al. 2012 Biotechnology and Bioengineering 109:1371-1375). This study investigated a CHO-K1 host, secreted alkaline phosphatase (SEAP)- and tissue plasminogen activator protein (tPA)-expressing CHO-K1-derived cell lines and found 173 conserved miRs of which 136 were differentially expressed in either the SEAP or tPA recombinant cell line and 75 in both compared to the host. Of those identified as differentially expressed were included miR-15a, -15b and -34c (Hammond et al. 2012 Biotechnology and Bioengineering 109:1371-1375). Another study reported that mmu-miR-446h expression influenced apoptosis in CHO cells (Druz et al. 2011 Biotechnology and Bioengineering 108:1651-1661). A study in CHO reported by Johnson et al. (2011) identified 350 miRs via alignment with known miRs from the miRBase database (Johnson et al. 2011 Biotechnology and Bioengineering 108:475-480). This study showed (i) that almost all mature miRs in the CHO cell lines investigated were highly homologous to their human or mouse counterpart; and (ii) that the expression of many of the miRs changed in response to small environmental perturbations. This study also reported that hamster miR cgr-let-7f is the most abundant miR in CHO cells and its levels were comparable across the conditions investigated.

A similar sequencing approach was reported by Hackl et al. (Hackl et al. 2011 Journal of Biotechnology 153:62-75) to identify and annotate both conserved and novel miRs in CHO cells. At the time of the study, the authors had no access to an annotated CHO genome. Instead, read alignment patterns and read count ratios of 5' and 3' mature miRs were obtained and used for an independent classification into miR/miR* and 5p/3p miR pairs and discrimination of miRs from other non-coding RNAs, resulting in the annotation of 387 mature CHO miRs. The study included a comparison of serum vs serum-free conditions and host vs derivative recombinant cell lines. In the host vs recombinant derivative cell line comparison they reported differential expression of miR-16b (Hackl et al. 2011 Journal of Biotechnology 153:62-75). The same group has also reported on the expression of miRs in CHO-K1 suspension cell cultures at different phases of batch culture and report that more than 100 miRs were differentially regulated across batch culture (Hernandez Bort et al. 2012 Biotechnology Journal 7:500-515). In another study, Lin et al (2011) investigated miR levels in host CHO DG44 cells and a derivative IgG-producing cell line, reporting that miR-221 and miR-22 were down-regulated in the IgG-producing recombinant cell lines. However, there was no relationship between the concentration of IgG secreted into culture medium and expression of these miRs. In the parental DG44 cell line, miR-15b expression was also significantly lower compared to a derivative cell line producing a recombinant protein (Lin et al. 2011 Biotechnology Progress 27:1163-1171).

One of the first reports into miR expression in CHO cells was that from Gammell et al. (Gammell et al. 2007 Journal of Biotechnology 130:213-218). The approach taken by the authors was to use a non-hamster microarray and investigate miR expression upon temperature-shift. The resulting data showed that miR-21 and miR-24 were up-regulated in CHO-K1 growth-arrested cell lines, induced either by temperature shift or during normal batch culture (US 2010/0190258 A1). Subsequently, this group reported that lowering the temperature from 37° C. to 28-33° C. led to increased levels of miR-219, miR-518d, miR-126, miR-30e, miR-489 and miR-345, when measured after 24 h, while miR-7, miR-320, miR-101 and miR-199 were down-regulated (Barron et al. 2011 Journal of Biotechnology 151:204-211). The successful exogenous over-expression of miR-7 resulted in a blocking of cell proliferation and increased normalised (per cell) recombinant protein production at 37° C. but the yield was still lower than from cells at reduced temperature.

The impact of miR manipulation is often investigated using reporter genes and 'sponge vectors' (Ebert et al. 2007 Nature Methods 4:721-726). In order to demonstrate the influence of miRs on industrially-relevant phenotypes it is necessary to validate this by either reducing or increasing expression of the miR in question. Jadhav et al. (Jadhav et al. 2012 Biotechnology and Bioengineering 109:1376-1385) recently reported that the functional analysis of miRs in CHO cells can be successfully demonstrated using a recombinant EPOFC-producing CHO cell line and transient transfection over a four day period.

Commercial recombinant protein production often requires large-scale manufacturing processes. Despite recent advances in industrial processes, recombinant protein production remains a challenging task. Therefore there is still the need to provide further improved means and methods for the production of proteins in a more efficient and optimised way.

The present invention is inter alia based on the technical problem to provide improved or further means and methods for the industrial scale production of proteins.

The present invention solves its technical problem by the provision of the teaching of the independent claims.

In particular, the present invention solves its technical problem by providing a method for the production of a protein of interest in a mammalian producer cell comprising the process steps
  a) providing a mammalian producer cell,
  b) increasing the concentration of at least one miR selected from the group consisting of miR-15, miR-16 and miR-34 in the mammalian producer cell provided in step a) so as to obtain a protein production engineered mammalian producer cell,
  c) cultivating the protein production engineered mammalian producer cell under conditions suitable for the production of the protein of interest, and
  d) recovering the protein of interest produced in step c).

The present invention, thus, increases the concentration, that means raises the amount, in particular intracellular amount of the identified miRs in a mammalian producer cell to provide for an increased production of the protein of interest.

In the context of the present invention the term concentration is understood to also mean level.

In the context of the present invention, an increased concentration of a miR is a higher concentration of said miR compared to the concentration of said miR in the mammalian producer cell provided in step a). The concentration of miR can be determined by conventional methods to determine miR amounts in a cell, for instance by qRT-PCR-analysis. Appropriate control measurements and the establishment of appropriate standards are known to the skilled person.

In the context of the present invention an increased production of the protein of interest is meant to refer to a higher specific production rate (qP) of the protein of interest, in particular the recombinant protein of interest in the cell and/or to a higher time integral of viable cell concentration (IVC). Recombinant protein production or productivity, being defined as concentration of the said protein in the culture medium, is a function of these two parameters (qP and IVC), calculated according to Porter et al. (Porter et al. 2010 Biotechnology Progress 26:1446-1455).

Methods of measuring increased protein production are well-known to those skilled in the art. For example, an increase in recombinant protein production might be determined at small-scale by measuring the titre in tissue culture medium by ELISA (Smales et al. 2004 Biotechnology Bioengineering 88:474-488). It can also be determined quantitatively by the ForteBio Octet, for example for high throughput determination of recombinant monoclonal antibody (mAb) concentration in medium (Mason et al. 2012 Biotechnology Progress 28:846-855) or at a larger-scale by protein A HPLC (Stansfield et al. 2007 Biotechnology Bioengineering 97:410-424). Methods for counting cells include, but are not limited to, trypan blue exclusion methods followed by counting using a haemocytometer or Vi-CELL (Beckman-Coulter).

Said increased production of the protein of interest may in one embodiment be due to an increased specific protein production rate (qP) of the cells as a result of the increased intracellular concentration of the at least one miR obtained in step b) of the present process. In one embodiment, said increased protein production may alternatively or additionally be due to increased cell growth, in particular a higher IVC as a result of the increased concentration of the at least one miR obtained in step b) of the present process. Thus, the present invention is particularly useful for the growth and use of mammalian producer cells, in particular cell lines, which are used in the generation of proteins, in particular recombinant proteins.

In accordance with the present invention, step a) of the present method requires the provision of a mammalian producer cell, which means a cell that is capable of producing a protein of interest, in particular a recombinant protein of interest, and which is capable of being subjected to steps b) and c) of the present method.

In a preferred embodiment of the present invention, the protein of interest is an endogenous protein of the producer cell line.

In a further preferred embodiment, the protein of interest is exogenous to the producer cell. That means the protein of interest is not normally present in the producer cell. Thus, a nucleotide sequence encoding the protein of interest has to be introduced, in particular transfected, into the producer cell by methods known to the skilled person, preferably as mentioned below.

In a particularly preferred embodiment of the present invention, a nucleotide sequence encoding the protein of interest is transfected prior to step a) or x) of the present method. That means the exogenous protein of interest is already present in the provided producer cell. Preferably, the nucleotide sequence encoding the protein of interest is present on a vector or stably integrated in the genome of the producer cell.

In accordance with the present invention, step b) of the present method requires the increase in the concentration of at least one of said miRs in comparison to the level of said miR present in the mammalian producer cell before having carried out step b) so as to obtain a manipulated (engineered) mammalian producer cell, in the following also termed "protein production engineered mammalian producer cell". Said protein production engineered mammalian producer cell subsequently is cultivated in step c) under conditions suitable for the production of the protein of interest, wherein during said cultivation said protein of interest is produced and can be recovered, in particular can be separated from the culture medium and the cell.

In a further particularly preferred embodiment, a nucleotide sequence encoding the protein of interest is transfected into the producer cell simultaneously with the at least one miR during step b) or y) of the present process. Thus, in this embodiment, not only the concentration of the at least one miR is increased but also that of the protein of interest. Also here, the nucleotide sequence encoding the protein of interest can be on a separate vector or be stably integrated into the genome of the protein production engineered mammalian producer cell obtained.

In a still further particularly preferred embodiment, a nucleotide sequence encoding the protein of interest is transfected into the protein production engineered mammalian producer cell, i.e. after step b), y) or z) but before step c) of the present process.

In a particularly preferred embodiment, the cell culture is carried out as a batch culture, fed-batch culture or a continuous culture. Furthermore preferred, the cell culture is carried out as suspension culture. Preferably, a conventional cell culture medium is used in step b).

In a preferred embodiment, step b) of the present invention is carried out in a conventional cell culture medium, preferably a cell culture medium such as used in step c). In another embodiment of the present invention, step b) is carried out in a transfection medium, in particular a medium suitable for transfecting miRs or vectors comprising nucleotide sequences encoding miRs, and possibly the protein of interest, into the mammalian producer cell.

Suitable cultivation and recovery methods are known to the skilled person and may depend upon the protein of interest and the mammalian producer cell employed.

In a preferred embodiment, the protein of interest produced in step c) is recovered in step d) by isolating, preferably purifying, the protein of interest from the other components, preferably from the protein production engineered mammalian producer cell, present during the cultivating step c). The protein of interest obtained after the recovering according to step d) is substantially free, preferably free of the protein production engineered mammalian producer cell.

For recovering the protein of interest a physical or chemical or physical-chemical method is used. The physical or chemical or physical-chemical method is preferably a filtering method, a centrifugation method, an ultracentrifugation method, an extraction method, a lyophilization method, a precipitation method, a chromatography method or a combination of two or more methods thereof. The chromatography method is preferably selected from the group consisting of a size exclusion chromatography method, a hydrophobic interaction chromatography method, an ion exchange chromatography method, an affinity chromatography method and a metal binding chromatography method.

The present invention solves its technical problem also by providing a method for the preparation of a protein production engineered mammalian producer cell capable of expressing a protein of interest, comprising the process steps x) providing a mammalian producer cell,
y) increasing the concentration of at least one miR selected from the group consisting of miR-15, miR-16 and miR-34 in the mammalian producer cell provided in step x) so as to obtain a protein production engineered mammalian producer cell,
z) recovering the protein production engineered mammalian producer cell produced in step y).

The present method for the preparation of a protein production engineered mammalian producer cell, thus, provides for the production of an engineered mammalian producer cell which is preferably capable of increased specific protein production rate and/or capable of improved, in particular increased, cell growth, i.e. a higher time integral of viable cell concentration (IVC).

miR-15b and miR-16 are both apoptosis-inducing miRs, targeting mRNA encoding anti-apoptotic proteins such as Bcl2. Several other genes have also been revealed as targets for these miRs. For example, miR-16 is also reported to regulate Cyclin D1, Cyclin D3, Cyclin E1 and CDK6 causing cells to go into arrest at the G0/G1 phase of the cell cycle. miR-21 is another apoptotic inducing miR preventing cell proliferation and inducing cell death. miR-21, like miR-15 and miR-16, targets Bcl2 mRNA. miR-34c is involved in cell proliferation, mainly in p53-mediated apoptosis making it a key target for cancer diagnosis and therapy. miR-34 is a tumour suppressor, achieving this by targeting Notch, HMGA2, silent information regulator 1 (SIRT1) as well as Bcl-2 and other genes associated with tumour formation and/or development.

The present invention, thus, provides in an advantageous manner means and methods to enhance protein production, in particular to allow the large-scale production of a protein of interest in a mammalian producer cell. The present invention also provides improved mammalian producer cells, that means engineered mammalian producer cells, which are engineered so as to allow in a preferred embodiment, an improved, in particular, increased, protein production and/or improved, in particular increased, cell growth.

In the context of the present invention, the term "protein of interest" is meant to refer to an oligopeptide or polypeptide in glycosylated, partially glycosylated or non-glycosylated form.

The term "protein of interest" as used herein in singular form is also referring in one embodiment to at least one protein of interest, in particular polypeptides of interest, that means inter alia to two, three or more different proteins of interest. In one embodiment of present invention, the term "protein of interest" refers to one specific protein whose production is increased, preferably specifically increased, in particular merely the production of this specific protein is increased. In a particular and preferred embodiment, said protein of interest, in particular the nucleotide sequence encoding it, may be an endogenous or exogenous protein with respect to the mammalian producer cell, i.e. the mammalian host cell. In case the producer cell line comprises an exogenous protein of interest it is termed transgenic.

In the context of the present invention, the term "endogenous" protein refers to a protein already being present in or being encoded in the genome of the mammalian producer cell line and therefore is not originating from outside of said cell line.

In the context of the present invention, the term "exogenous" protein refers to a protein being present in said mammalian producer cell due to methods of recombinant gene technology, for instance conventional genetic engineering methods, preferably by means of transformation, electroporation or transfection of a nucleotide sequence encoding said exogenous protein, wherein said exogenous nucleotide sequence was, prior to that genetic engineering step, not present in said mammalian producer cell.

The protein of interest may be a genetically engineered, in particular a recombinant protein. In particular, the protein may be a biopharmaceutical.

In particular, the protein may be a mammalian, bacterial, viral or plant protein. Preferably, the protein is a human or humanised protein.

In a particularly preferred embodiment, said protein of interest can be an antibody, in particular a mAb, an antigen, a hormone, an enzyme, cytokine, a growth factor, a reporter protein, a selectable marker, e.g. the GS-selection marker, the hygromycin-selectable marker, the puromycin-selection marker or the thymidine kinase-selectable marker or a structural and/or functional part or hybrid of any of these.

In a particularly preferred embodiment, said protein of interest can be an antibody, in particular a mAb, an antigen, an enzyme, cytokine, a growth factor, a reporter protein, a selectable marker, e.g. the GS-selection marker, the hygromycin-selectable marker, the puromycin-selection marker or the thymidine kinase-selectable marker or a structural and/or functional part or hybrid of any of these.

In a preferred embodiment, the protein of interest may be a mAb, recombinant or chimeric antibody, or a fragment thereof, e.g. a heavy or light chain or a variable or constant region of an antibody. In a further preferred embodiment, the protein of interest may be growth hormone, insulin, FSH (follicle-stimulating hormone), factor VIII, TPO, EPO (erythropoietin), G-CSF, GM-CSF, TPA (tissue-plasminogen activator), interferon α, β or γ, insulin-like growth factor or somatrotropin.

In a preferred embodiment, the protein of interest may be a mAb, recombinant or chimeric antibody, or a fragment thereof, e.g. a heavy or light chain or a variable or constant region of an antibody. In a further preferred embodiment, the protein of interest may be growth hormone, FSH (follicle-stimulating hormone), factor VIII, TPO, EPO (erythropoietin), G-CSF, GM-CSF, TPA (tissue-plasminogen activator), interferon α, β or γ, insulin-like growth factor or somatrotropin.

In a preferred embodiment of the present invention, the protein production engineered mammalian producer cell comprises, preferably expresses, genes encoding Sox6 or Bhlhe22 or both. In a preferred embodiment the protein production engineered mammalian producer cell is free of genes encoding for Sox6 or Bhlhe22 or both. Preferably, the expression of the genes encoding for Sox6 or Bhlhe22 is suppressed partially or entirely in the protein production engineered mammalian producer cell.

The term "nucleotide sequence" or "polynucleotide" as used herein refers preferably, to nucleic acids, in particular nucleic acid molecules, preferably a DNA or RNA.

In the context of the present invention, the term "mammalian producer cell" is meant to refer to a mammalian cell, in particular a mammalian host cell, capable of producing a protein of interest, in particular to a mammalian host cell capable of producing a protein of interest and capable of being subjected to the process steps b) and c) or y) of the present methods.

In the context of the present invention, the term "a protein production engineered mammalian producer cell" is meant to refer to an engineered mammalian producer cell which is a result of having increased the concentration of at least one miR selected from the group consisting of miR-15, miR-16, miR-34 in the provided mammalian producer cell and which is therefore characterised by an increased concentration of said at least one miR, in particular two of said miRs, preferably three of said miRs in comparison to the mammalian producer cell provided in step a) or x). The present "protein production engineered mammalian producer cell" is characterised in one preferred embodiment by increased protein production, in one embodiment by an increased qP or IVC and in one embodiment by both of said characteristics.

In a preferred embodiment of the present invention, the "protein production engineered mammalian producer cell" is a cell exhibiting increased qP or an increased IVC or both.

In a preferred embodiment, the miR-15 is miR-15a or miR-15b. In a preferred embodiment, the miR-16 is miR-16-1 or miR-16-2.

In a preferred embodiment the miR-34 is miR-34a, miR-34b or miR-34c.

In a preferred embodiment, the concentration of the at least one miR is increased by transfecting the mammalian producer cell in step b) or y) with at least one miR selected from the group consisting of miR-15, miR-16 and miR-34.

Thus, in a preferred embodiment the mammalian producer cells are transfected with at least one miR or pre-miR, preferably at least two, most preferable three miRs or pre-miRs as identified herein, so as to obtain an increased concentration thereof. In a preferred embodiment, the producer cells are transiently transfected with at least one pre-miR encoding vector(s) whilst in another preferred embodiment cell lines are constructed which stably express at least one pre-miR(s), that means the protein production engineered producer cells contain the nucleotide sequence of at least one pre-miR stably integrated into their genome.

In a preferred embodiment, the concentration of at least one miR is increased by transfecting the mammalian producer cell in step b) or y) with at least one vector containing a nucleotide sequence encoding at least one miR under control of at least one regulatory element allowing the over-expression of at least one miR, wherein the at least one miR is selected from the group consisting of miR-15, miR-16 and miR-34.

In a preferred embodiment, the vector containing the nucleotide sequence coding at least one of the miRs is an expression vector.

Thus, in a preferred embodiment, the mammalian producer cells are transfected with at least one of the present vectors allowing in the transfected cells the over-expression of at least one miR, preferably at least two, most preferable three, miRs as identified herein, so as to obtain an increased concentration thereof. In a preferred embodiment of the present invention, the concentration is transiently increased. In another preferred embodiment of the present invention, the concentration is stably increased.

A regulatory element allowing the over-expression of at least one miR can be a promoter or any other expression promoting or expression enhancing element such as an enhancer. In a preferred embodiment, the regulatory element allowing the over-expression of at least one miR is a promoter, preferably a mammalian or viral promoter.

In a particularly preferred embodiment, the promoter may be a constitutive or inducible promoter, for instance a temperature-inducible promoter.

In a preferred embodiment, the at least one vector used in step b) or y) is transiently or stably transfected into the mammalian producer cell.

In a preferred embodiment, at least two, preferably i) miR-15 and miR-16 or ii) miR-15 and miR-34 or iii) miR-16 and miR-34, preferably all three, of the miRs or nucleotide sequences encoding at least two, preferably three, of the miRs are transfected.

In one preferred embodiment, at least two miR encoding nucleotide sequences may be transfected on the same vector. In another embodiment, the co-transfection of at least two miRs encoding nucleotide sequences is carried out with each individual miR encoded on separate vectors. Further, if the protein of interest is transfected together with the at least one miR it can be encoded on the same vector or on an individual vector.

The transfection of the nucleotide sequence encoding the at least one miR or of the at least one miR can be achieved using conventional methods well-known to the skilled person. Said methods may preferably be lipofectamine transfection, electroporation, liposome-mediated transfection, calcium-phosphate-mediated transfection, virus mediated transfection or direct gene transfer, e.g. particle bombardment.

In a preferred embodiment of the present invention, the nucleotide sequence encoding at least one miR, preferably at least one pre-miR under control of at least one regulatory element allowing the over-expression of at least one miR is transiently or stably contained in the mammalian producer cell.

In a preferred embodiment, the miR is a mature miR, a precursor miR (pre-miR) or a primary miR (pri-miR). The mature miR is preferably synthesised by the cell or is an exogenously-added chemically synthesised oligonucleotide.

In a preferred embodiment, the mammalian producer cell is preferably a rodent cell, a hamster cell, a mouse cell or a human cell, a Y0 cell, a COS cell, a sp2/0 cell, a CHO cell, a CHO-K1 cell or a CHO-K1SV cell, a DG44 CHO cell, a DUXB11 CHO cell, a CHO GS knock-out cell, a CHO FUT8 GS knock-out cell, a NS0 cell, a PERC6 cell, a HEK293 cell, a HT1080 cell or a BHK cell. The mammalian producer cell can also be a baby hamster kidney cell (BHK) cell. The producer cell can also be a non-mammalian cell, e.g. an insect cell etc., preferably the producer cell is a non-human cell.

In a preferred embodiment, the mammalian producer cell is a CHO cell, a NS0 cell, a PERC6 cell, a HT1080 cell or a baby hamster kidney (BHK) cell. In a preferred embodiment, the CHO cell is selected from the group consisting of a CHO-K1 cell, a CHO-K1SV cell, a DG44 CHO cell, a DUXB11 CHO cell, a CHO GS knock-out cell and a CHO FUT8 GS knock-out cell.

The CHO GS knock-out cell is preferably a CHO-K1SV GS knockout cell, preferably GS Xceed™ of Lonza. The CHO FUT8 knockout cell is preferably the Potelligent® CHOK1SV of Lonza.

In the context of the present invention, the term "cell" is meant to refer to a single cell. The term "cell" is also meant to refer to a cell line, preferably an immortalised cell line, which may comprise a pool of cells.

The present invention solves its technical problem also by providing a "protein production engineered mammalian producer cell" produced according to anyone of the methods of the present invention.

The present invention provides in particular a "protein production engineered mammalian producer" cell comprising at least one transgenic nucleic acid sequence encoding at least one miR, which transgenic nucleic acid sequence is transiently or stably incorporated into the genome of that cell under control of at least one regulatory element allowing the over-expression of said at least one miR, wherein the at least one miR is selected from the group consisting of miR-15, miR-16 and miR-34.

The present invention provides in particular a kit for the production of the protein of interest in a mammalian producer cell, comprising at least one mammalian producer cell, at least one vector containing a nucleotide sequence encoding at least one miR under control of at least one regulatory element allowing the over-expression of the at least one miR, wherein the miR is selected from the group consisting of miR-15, miR-16, miR-34 and means for transfecting the at least one cell with the at least one vector.

In a preferred embodiment, the kit further comprises a second vector comprising a nucleotide sequence encoding a protein of interest.

Further preferred embodiments are the subject matter of the sub-claims.

The present invention will now be explained in more detail by way of non-limiting examples and the accompanying figures.

The figures show:

FIG. 1. Batch growth curve of two recombinant GS-CHOK1SV cell lines expressing the mAb cB72.3 grown in CD-CHO medium (■='high' producer CHO 42 cell line with a mAb titre of 550±4 mg/L at the completion of shake flask batch culture, Δ='low' producer CHO 114 cell line with a mAb titre of 313±64 mg/L at the completion of shake flask batch culture). Samples were taken throughout batch culture at the times indicated by arrows for extraction of miR material from cell pellets for qRT-PCR analysis.

Figure 2:
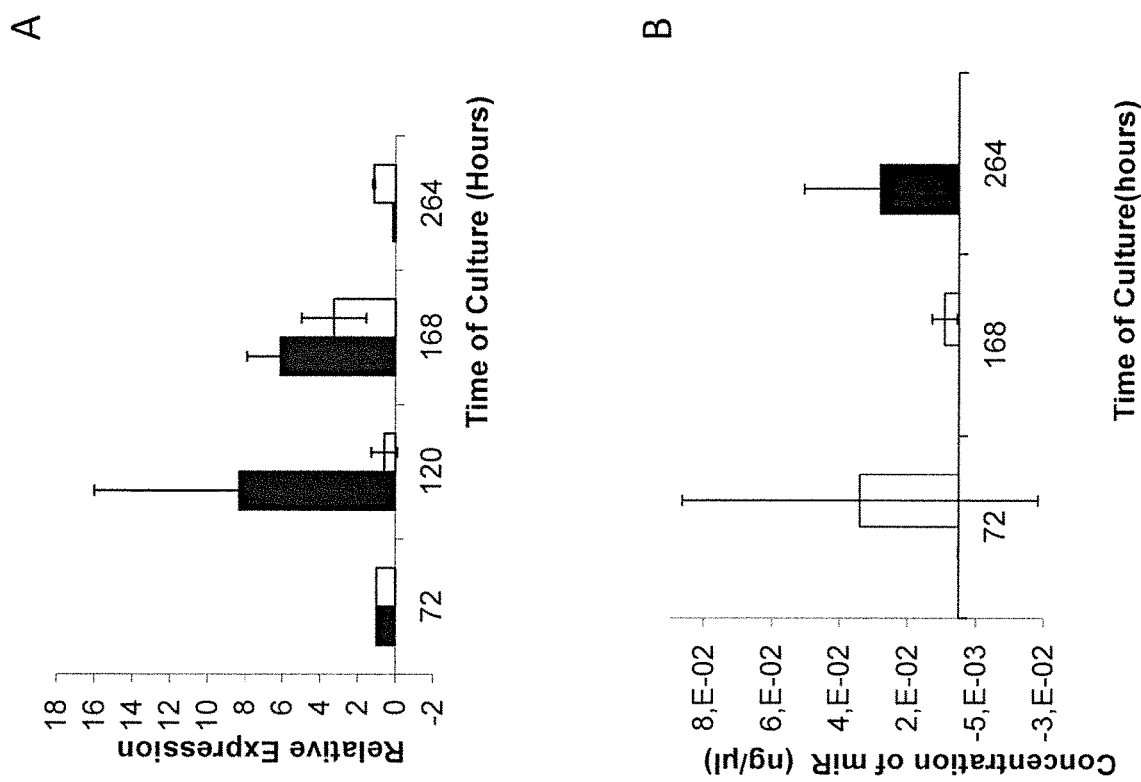

FIG. 2. The profile of pre-miR-15b (A) and mature miR-15b (B) throughout batch culture of the 'high' producer CHO 42 (■) and 'low' producer CHO 114 (□) cB72.3 mAb-producing GS-CHOK1SV cell lines. Error bars=±SD (n=3).

Figure 3:
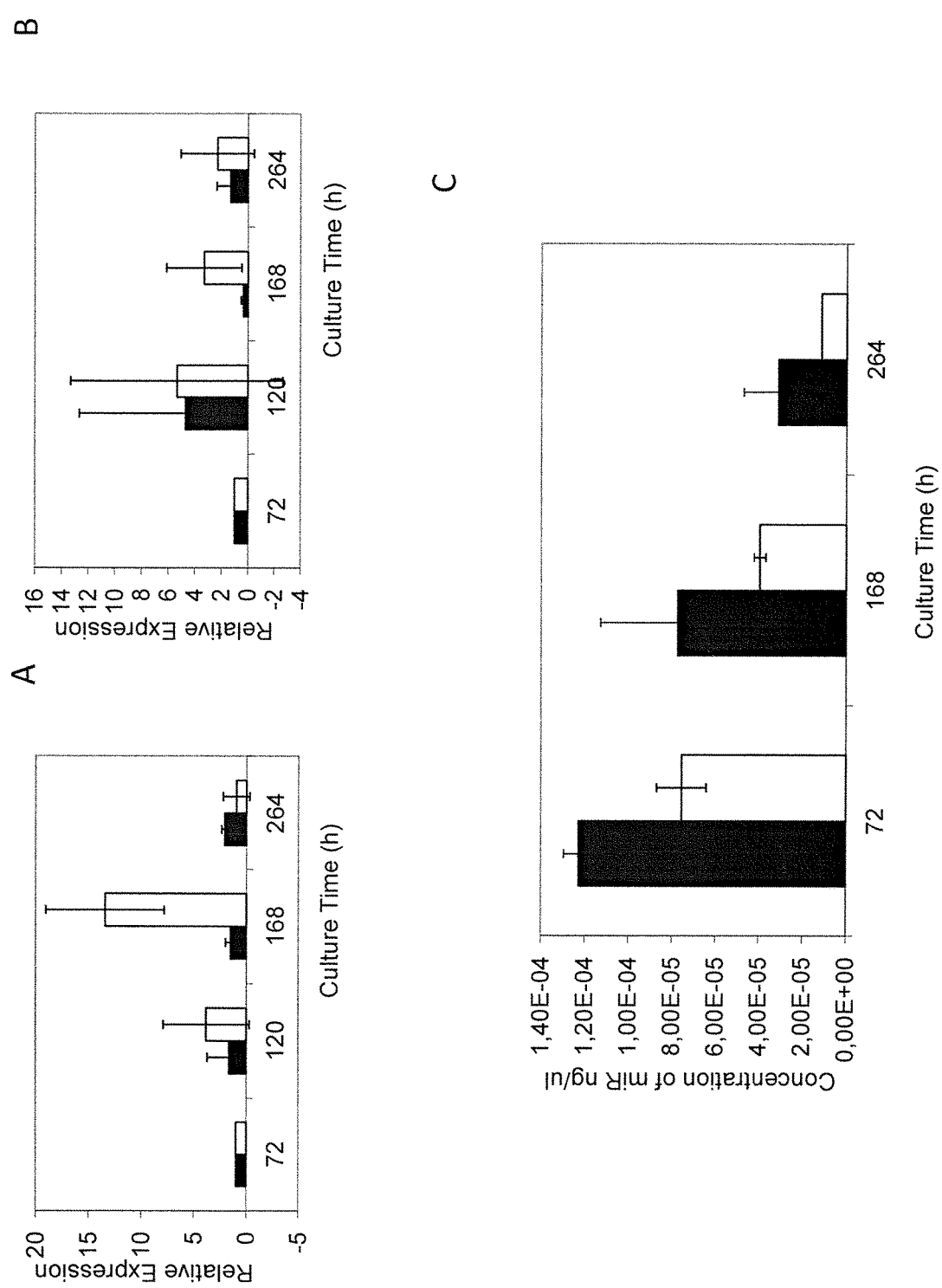

FIG. 3. The profile of (A) pre-miR-16-1, (B) pre-miR16-2 and mature (C) miR-16 throughout batch culture of the CHO 42 (■) and CHO 114 (□) cB72.3 mAb-producing GS-CHOK1SV cell lines. Error bars=±SD (n=3).

Figure 4:
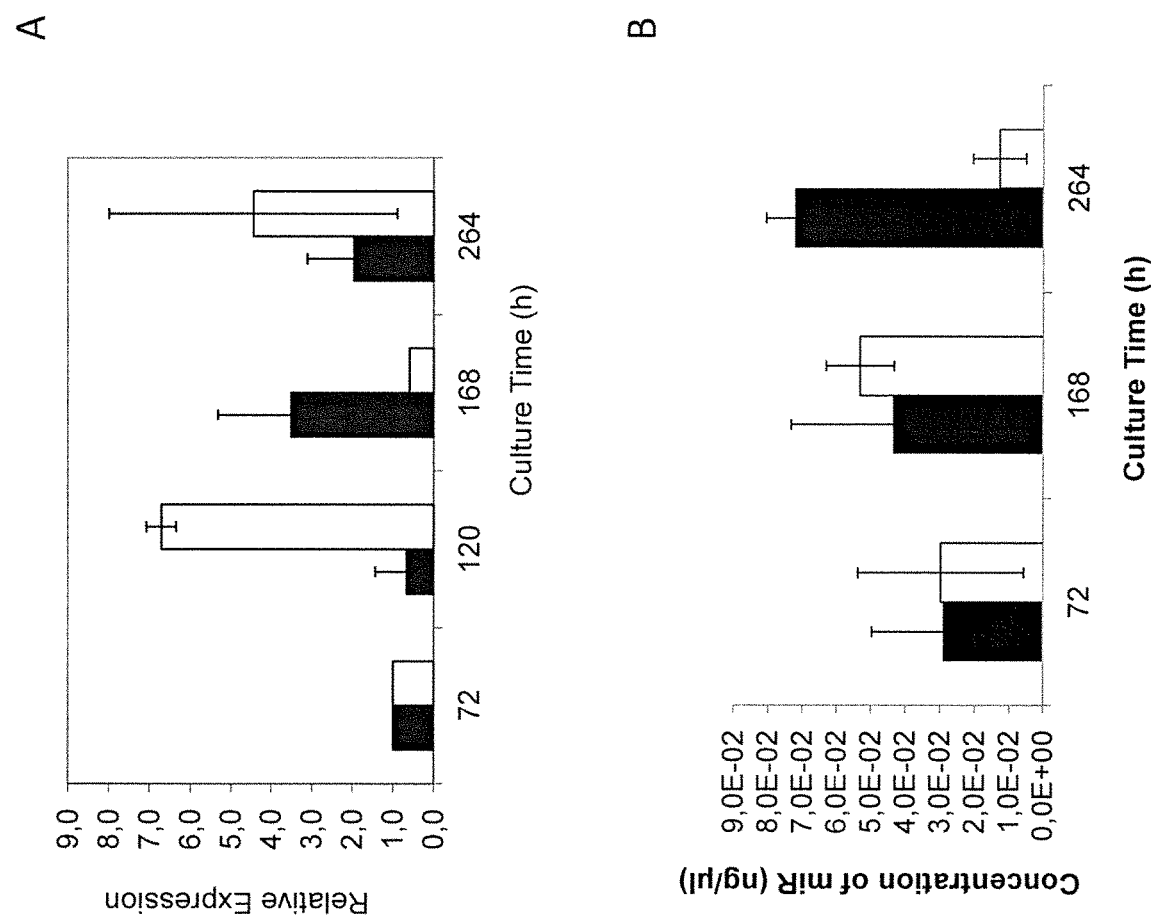

FIG. 4. The profile of (A) pre-miR-21 and (B) mature miR-21 throughout batch culture of the 'high' producer CHO 42 (■) and 'low' producer CHO 114 (□) cB72.3 mAb-producing GS-CHOK1SV cell lines. Error bars=±SD (n=3).

Figure 5:
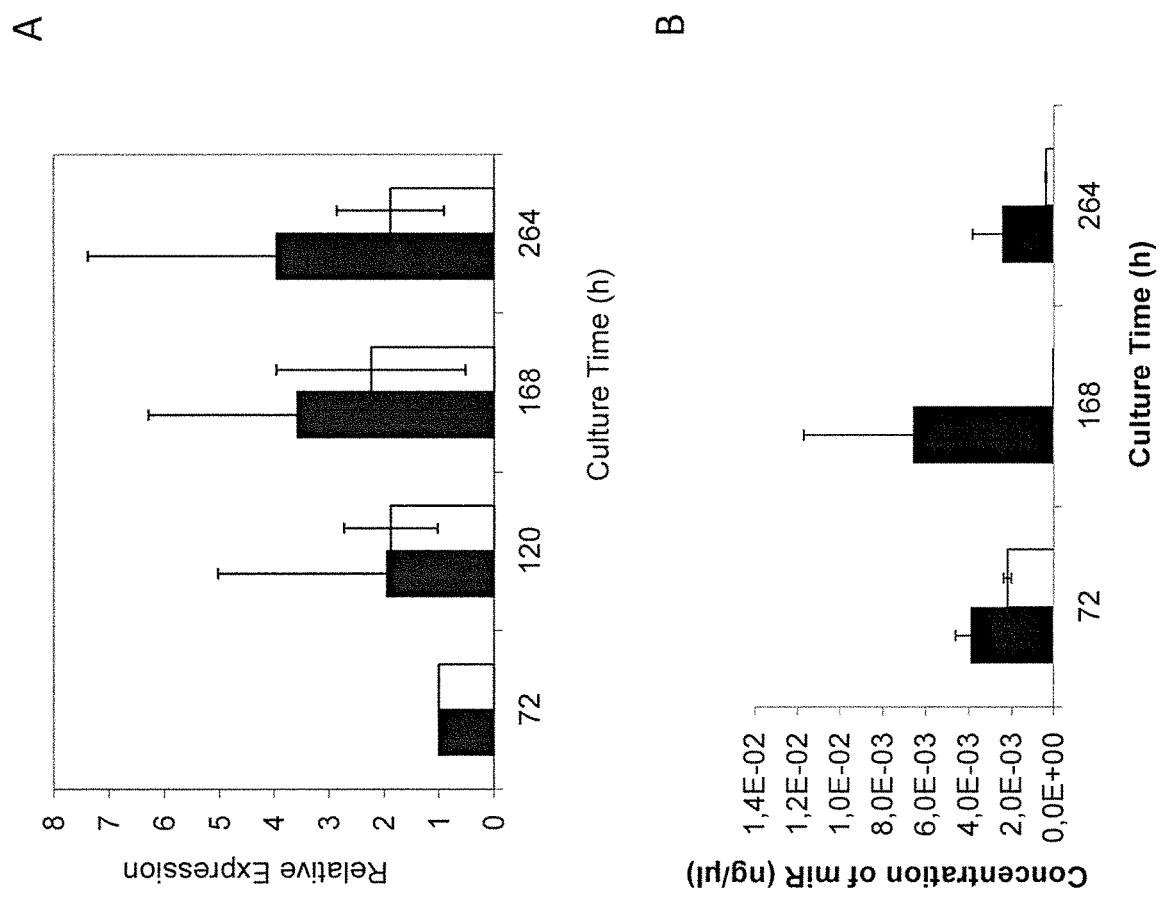

FIG. 5. The profile of (A) pre-miR-34c and (B) mature miR-34c throughout batch culture of the 'high' producer CHO 42 (■) and 'low' producer CHO 114 (□) cB72.3 mAb-producing GS-CHOK1SV cell lines. Error bars=±SD (n=3).

Figure 6:
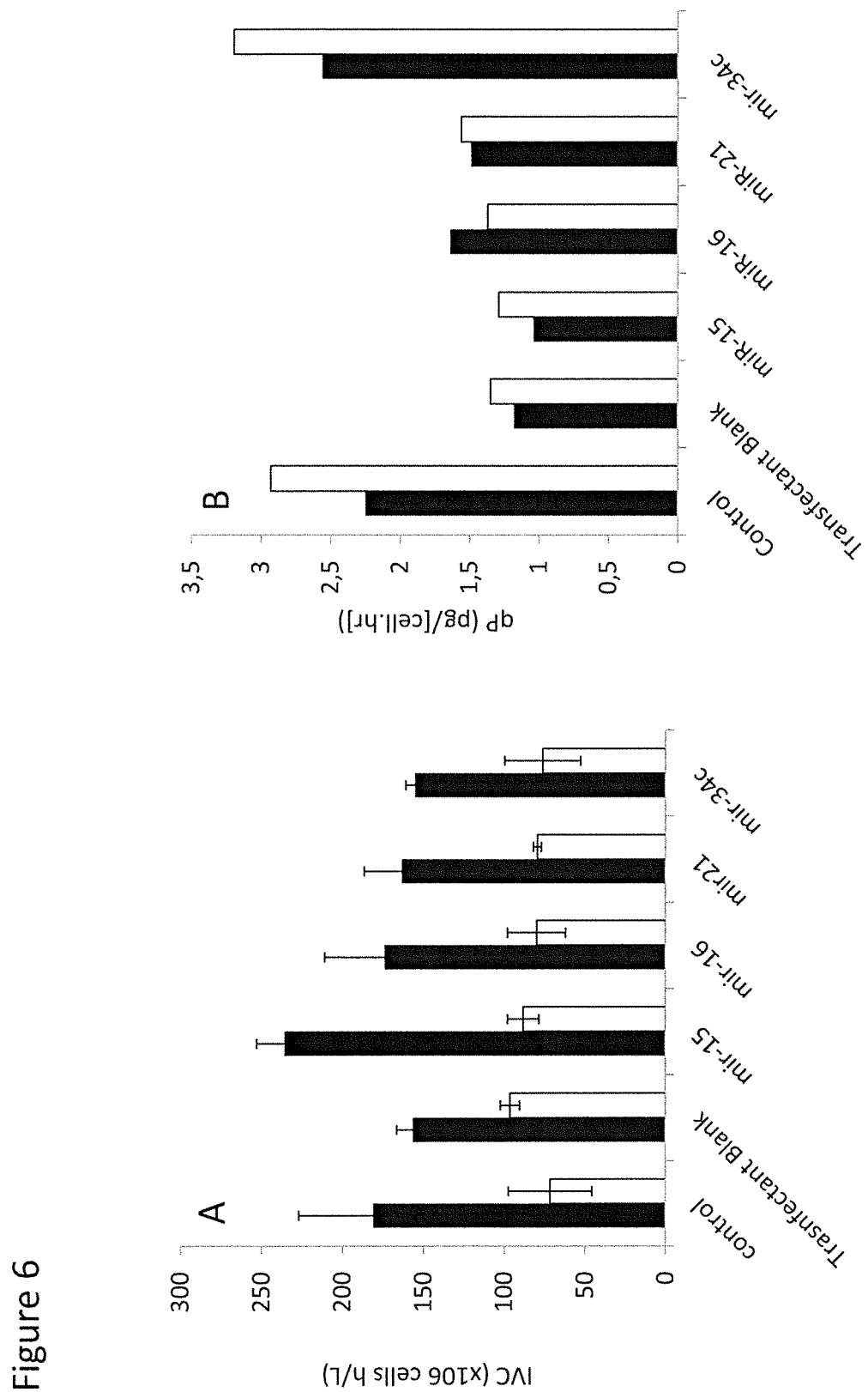

FIG. 6. Effect of transient over-expression of miRs on IVC and qP as determined over a period 24-96 h post-transfection for the 'high' producer CHO 42 (■) and 'low' producer CHO 114 (□) cB72.3 mAb-producing GS-CHOK1SV cell lines.

Figure 7:
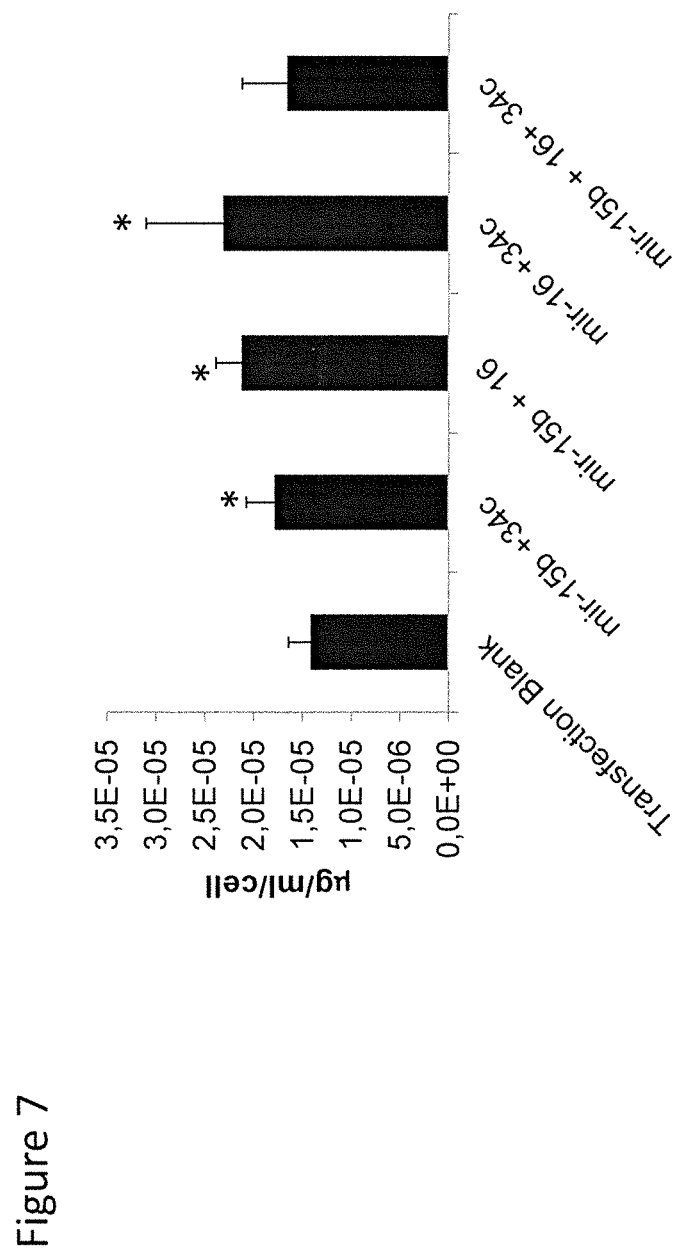

FIG. 7. Effect of transient over-expression of pre-miRs on the concentration of mAb in medium at 96 h post-transfection in the 'high' producer CHO 42 cB72.3 mAb-producing GS-CHOK1SV cell line. The mAb concentration has been normalised to the viable cell concentration of the culture at each time point. *=statistically significant increase in mAb expression (P<0.05) compared to the transfectant blank control. Error bars=±SD (n=3).

Figure 8:
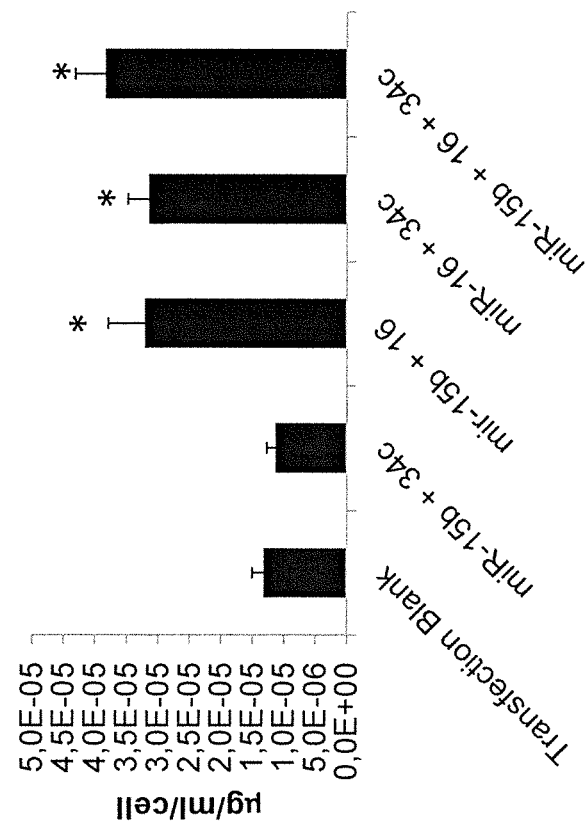

FIG. 8. Effect of transient over-expression of pre-miRs on the concentration of mAb in medium at 96 h post-transfection in the 'mid' producer CHO 56 cB72.3 mAb-producing GS-CHOK1SV cell line. *=statistically significant increase in mAb expression (P<0.05) compared to the transfectant blank control. Error bars=±SD (n=3).

Figure 9:
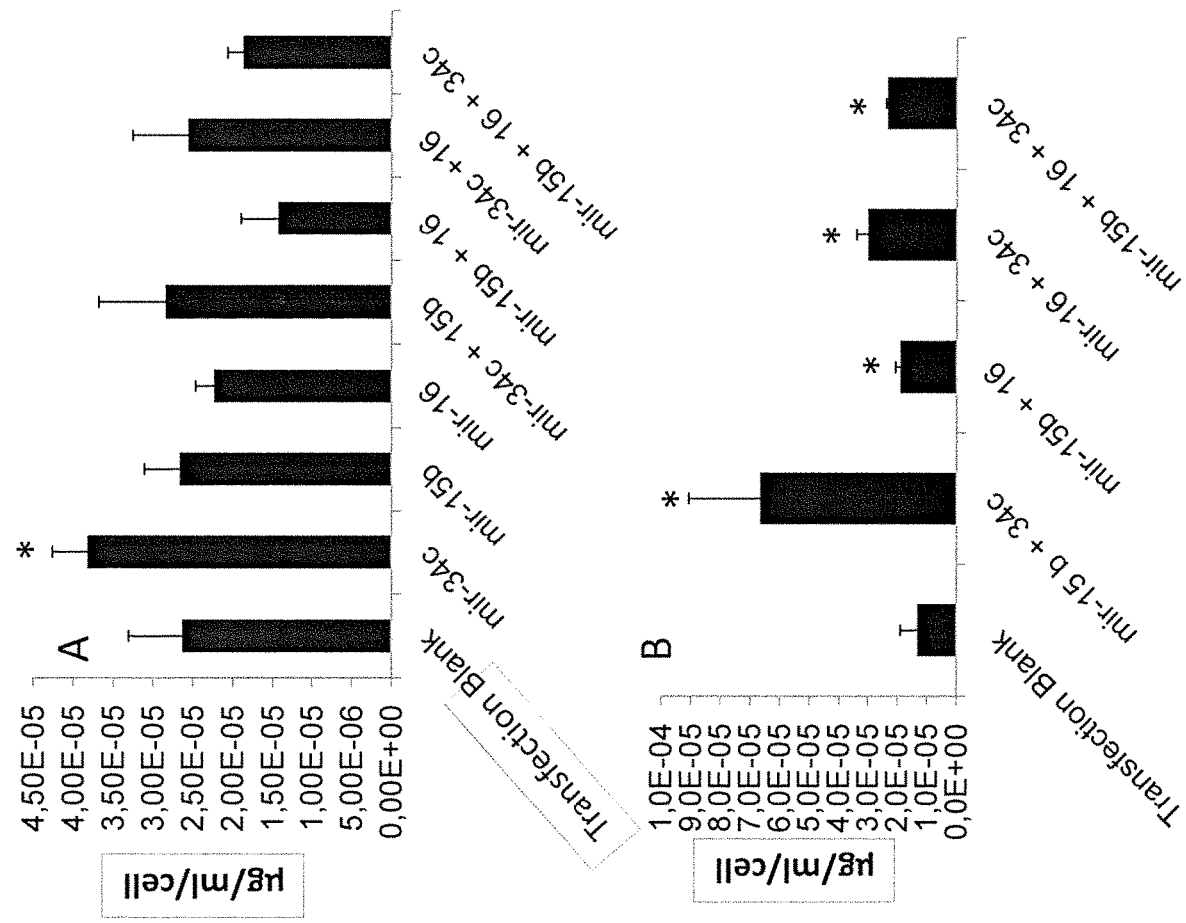

FIG. 9. Effect of transient over-expression of miRs on the concentration of mAb in medium at (A) 48 h and (B) 96 h post-transfection in the 'low' producer CHO 114 cB72.3 mAb-producing GS-CHOK1SV cell line. *=statistically significant increase in mAb expression (P<0.05) compared to the transfectant blank control. Error bars=±SD (n=3).

Figure 10:
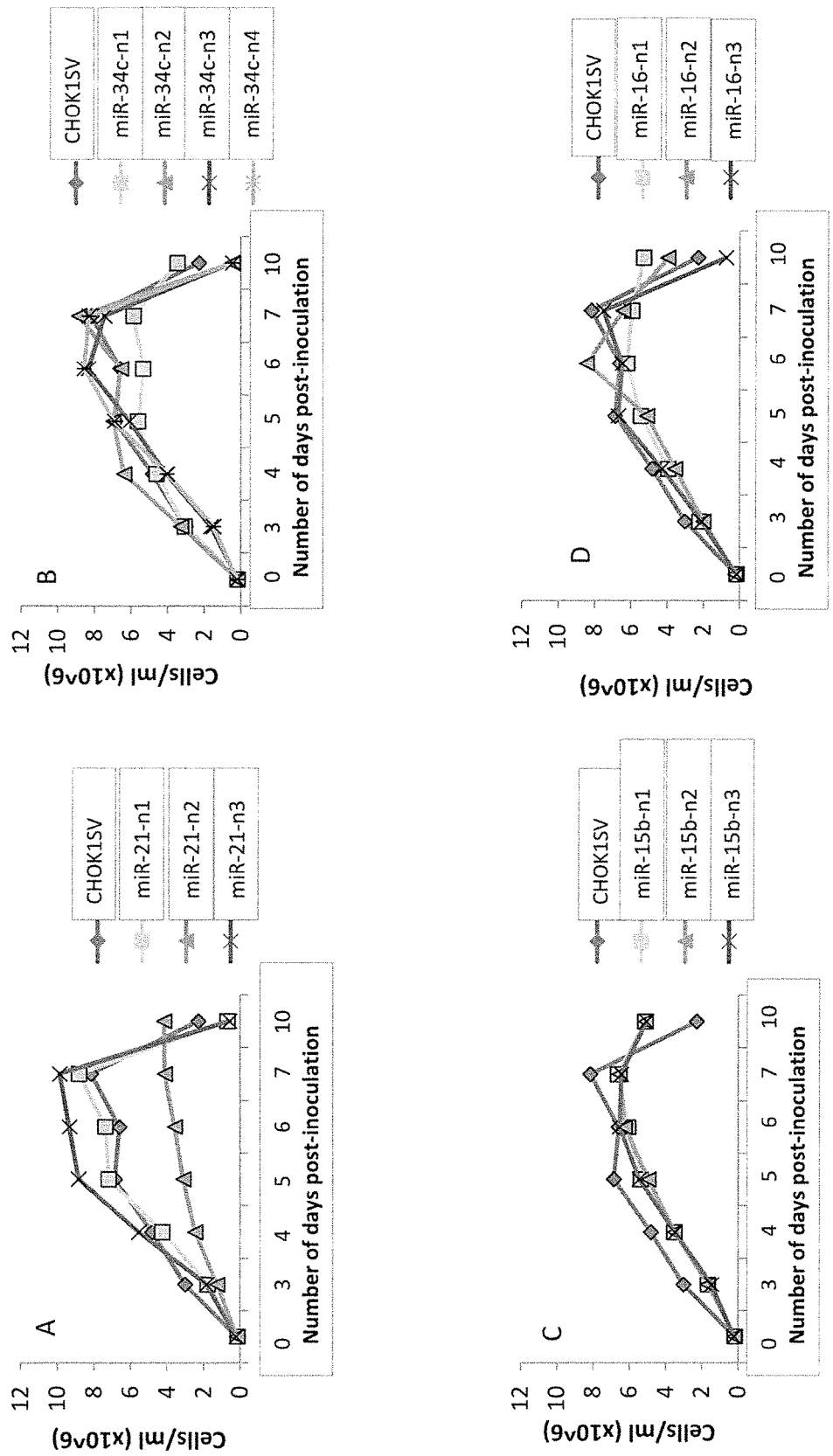

FIG. 10. Growth curves of CHOK1SV pools created by transfection with vectors encoding individual pre-miRs. Δ=miR-21 pool (pre-miR-21 encoding vector JR03), B=miR-34c pool (pre-miR-34c encoding vector JR04), C=miR-15b pool (pre-miR-15b encoding vector JR05), D=miR-16 pool (pre-miR-16 encoding vector JR06). Three cultures for each pool are shown alongside the CHOK1SV host.

Figure 11:
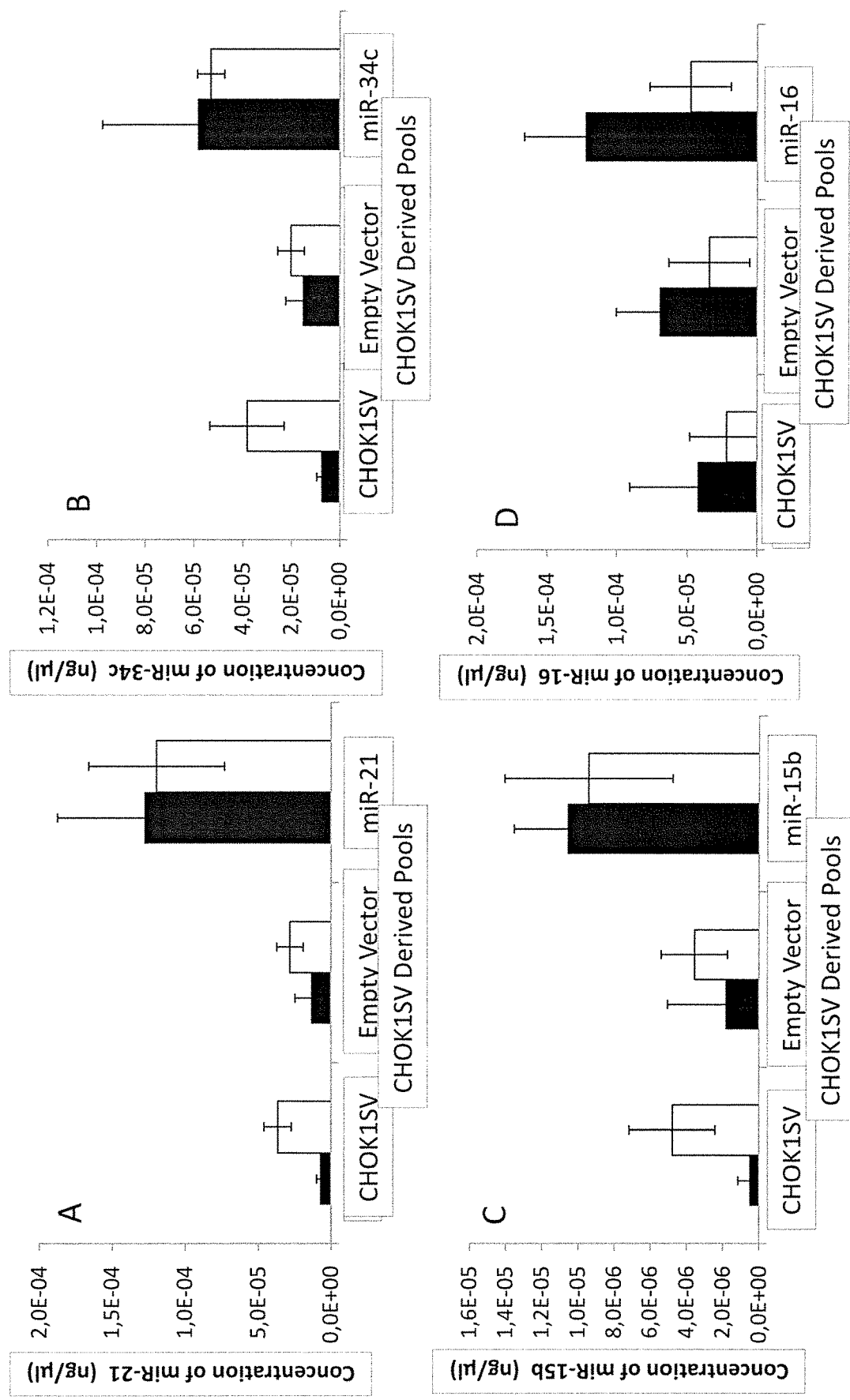

FIG. 11. Mature miR expression on day 5 (■) and day 7 (□) of batch culture of CHOK1SV-derived pools created by transfection with vectors encoding individual pre-miRs. Δ=miR-21 (pre-miR encoding vector JR03), B=miR-34c (pre-miR-34c encoding vector JR04), C=miR-15b (pre-miR-15b encoding vector JR05), D=miR-16 (pre-miR-16 encoding vector JR06) CHOK1SV host cell line, RY05=Pool created by transfection with miR expression vector encoding no miR. Error bars=±SD (n=3).

Figure 12:
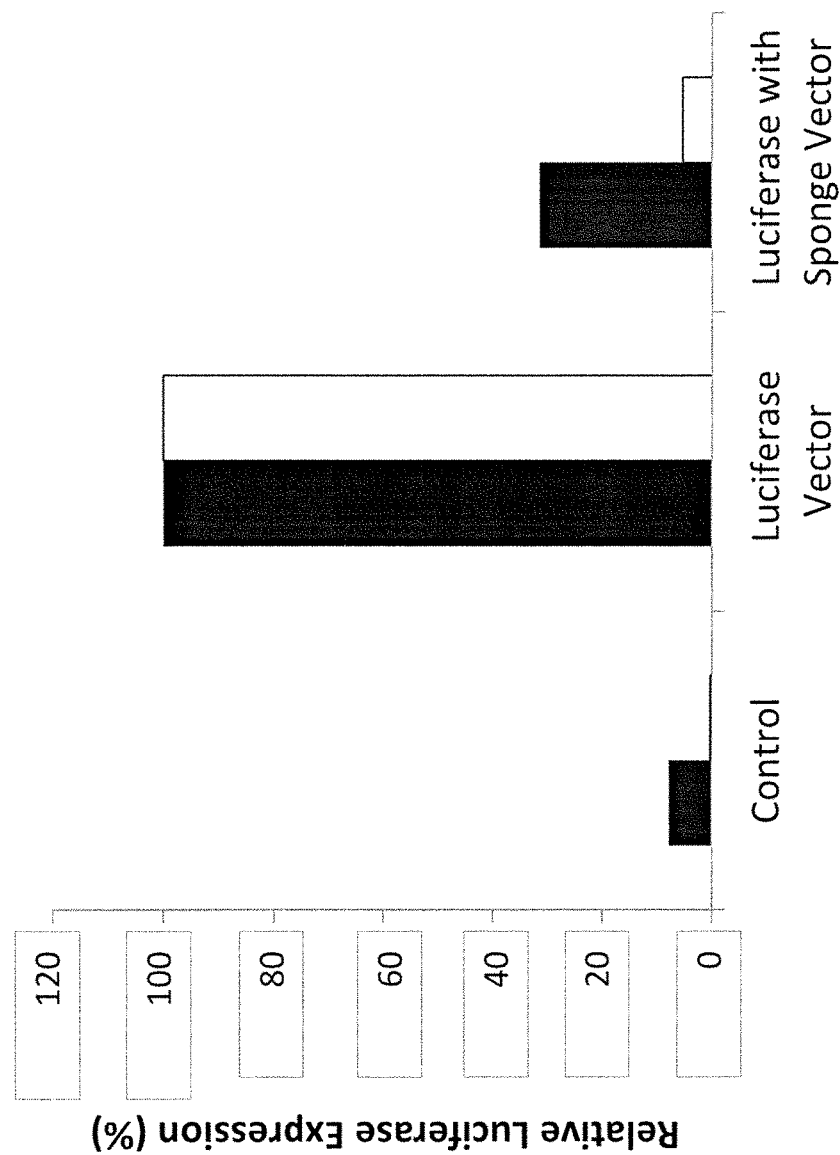

FIG. 12. Luciferase expression 48 h post-transient transfection in various miR-manipulated cell lines. (■) Pools were transfected with the luciferase reporter vector with or without the miR-34c target sequence (without=luciferase vector', with=luciferase with sponge vector' containing target sequence for miR-34c) in the 3'-UTR of the luciferase transcription unit. (□) Pools were super-co-transfected with additional miR-34c encoding vector plus either the luciferase reporter vector with the miR-34c target sequence in the 3'-UTR of the luciferase transcription unit or without it. All data is shown relative to the luciferase expression in the miR-34c stable pool in the absence of the target sequence for miR-34c.

Table 1 below identifies the nucleotide sequences of pre-miR primers (SEQ ID Nos 1 to 12) used in the present invention.

EXAMPLES

Materials and Methods

Vectors for Over-Expression of miRs and Sponge Vectors

Vectors for over-expression of miRs were generated to express the hairpin of the human miR—generating a pre-miR. A puromycin selection marker was included in the vector for the generation of stable cell lines. A sponge vector consisting of Renilla luciferase with a complementary or near complementary miR-34c target sequence in the 3'-UTR was used to show that over-expression of miR-34c results in gene silencing.

Cell Culture

CHO-K1 adherent cells (European Collection of Cell Culture) were cultured in Gibco® DMEM (Life Technologies, UK) supplemented with 500 µM L-glutamic acid and 500 µM asparagine, 200 mM L-glutamine, nucleosides (30 µM adenosine, cytidine, uridine and guanosine with 10 µM thymidine (all Sigma)), 10% (v/v) heat inactivated foetal bovine serum (PAA laboratories) and 1% (v/v) Gibco® nonessential amino acids (Life Technologies, UK). CHO-K1 was maintained in T-flasks (75 cm$^2$, Sartorius) at 37° C. in a humidified 5% $CO_2$ in air incubator. When the flask became approximately 80% confluent the cells were split. The current medium was aspirated and washed out with 10 mL phosphate buffered saline (PBS) (1 tablet per 100 mL of sterile water (Oxide Limited)). The PBS was aspirated and the cells were incubated in 3 mL of trypsin (Life Technologies, UK) for 2-3 min at 37° C., 5% $CO_2$ (v/v) in air. 10 mL of medium were then added to inhibit the trypsin and the cell suspension was poured into a 50 mL falcon tube and centrifuged for 5 min at 1000 rpm. The supernatant was then removed and the cell pellet resuspended in 10 mL of fresh media to confirm that the cell viability was >95% (as determined using a ViCell instrument). A new T75 flask containing 10 mL of fresh medium was then seeded by adding 0.25 mL of the cell suspension to the T75 flask.

GS-CHO 42, 56 and 114 suspension cells (Lonza Biologics plc) were cultured in CD CHO medium (Life Technologies, UK). These were routinely maintained in Erlenmeyer flasks at 37° C. in a humidified 5% $CO_2$ in air (v/v) orbital shaking incubator at 100 rpm and were initially seeded at $2 \times 10^5$ cells·mL$^{-1}$.

GS-CHO 42 and GS-CHO 114 Batch Cultures

Both cell lines were initially seeded at $3 \times 10^5$ cells·mL$^{-1}$ in 100 mL of CD CHO medium in large 500 mL Erlenmeyer flasks and incubated at 37° C. in a humidified 5% $CO_2$ in air (v/v) orbital shaking incubator at 100 rpm. A sample was taken daily for cell counting (1 mL). At time points of 3, 5, 7 and 11 days of culture time, aliquots of $1 \times 10^7$ cells were removed for miR analysis. Cells were harvested by centrifugation, the pellet washed once with PBS and stored at −70° C. The supernatant was retained in order to determine the concentration of secreted mAb.

RNA Extraction

RNA extraction was undertaken using the MirVANA RNA Extraction Kit (Life Technologies, UK) following the manufacturer's instructions. A Nanodrop instrument was used to measure the quantity of RNA obtained by determining the absorbance at a wavelength of A260 nm. A 20 ng·mL$^{-1}$ dilution of the RNA extract was prepared to use in the subsequent qRT-PCR. For miR analysis the manufacturer's protocol for the enrichment of small RNAs was followed.

qRT-PCR Analysis-TaqMan

All qRT-PCR materials were sourced from Applied Biosystems unless otherwise stated. For all experiments the two-step TaqMan® MicroRNA Assay kit was utilised with 48 and 96 well opaque plates and adhesive sheets (both obtained from Bio-Rad). The first step involves the miR Reverse Transcription kit and collected sample. Each well was prepared according to the manufacturer's instructions to contain 7 µL of master mix, 3 µL of the appropriate primer (which are provided in the kit, one for each miR) and 5 µL of RNA sample at a concentration of 10 ng·mL$^{-1}$. The RT-PCR was run on an Eppendorf Authorised Thermo Cycler using the following program:
- 16° C. for 30 min
- 42° C. for 30 min
- 85° C. for 5 min The second qRT-PCR step was then performed. Each well consisted of 1 µL of TaqMan microRNA Assay (20×), 1.33 µL of product from the first step, 10 µL TaqMan Universal PCR Mix and 7.67 µL nuclease-free water. The qRT-PCR experiments were run on a Mastercycler® Eppendorf Realplex$^4$ instrument using the following PCR cycle details;
1. 95° C. for 10 min
2. 95° C. for 15 seconds
3. 60° C. for 60 seconds
Steps 2 and 3 repeated for 40 cycles The products of the qRT-PCR were analysed on a 2% agarose gel alongside a 10 bp DNA ladder (Invitrogen).

To determine the copy number of each miR, a standard curve was generated using commercially synthesized material of each miR of known concentration. The standard curve was generated using the synthetic material in the TaqMan® MicroRNA Assay with known copy numbers and the subsequent unknown miR concentrations determined from samples using the standard curve.

qRT-PCR Analysis Using SYBR Green to Determine Relative Concentrations of Immature Pre-miR Between Time Points and Cell Lines For all experiments the SYBR Green one step qRT-PCR kit was utilised with 48 and 96 well opaque plates and adhesive sheets. Each well was prepared to contain 12.5 µL of SYBR green mix, 1.5 µL of the appropriate primers, 0.5 µL of RT enzyme, 2 µL of RNA at a concentration of 2.5 ng/mL and 8.5 µL of dd$H_2O$. The primers utilised during this study are described in Table 1 below.

qRT-PCR experiments were run on a Mastercycler® Eppendorf Realplex$^4$ instrument using the following PCR cycle details;
1. 50° C. for 10 min
2. 95° C. for 5 min
3. 95° C. for 10 seconds
4. 58° C. for 30 seconds
Steps 3 and 4 repeated for 40 cycles
    Melting Curve (measured at 0.5° C. change in temperature)

The products of the qRT-PCR were analysed on a 1% agarose gel alongside a 100 bp RNA ladder (Invitrogen, Life Technologies, UK).

TABLE 1

Primers Designed for pre-miR qRT-PCR experiment

| Gene | Forward Primer | Reverse Primer |
|---|---|---|
| Pre-miR-15b | AGTACTGTAGCAGC ACATCATGG (SEQ ID No 1) | TTTCCTTAAATTTC TAGAGCAGCA (SEQ ID No 2) |
| Pre-miR-16-1 | AGCAGTGCCTTAGC AGCAC (SEQ ID No 3) | CAACCTTACTTCAG CAGCACA (SEQ ID No 4) |
| Pre-miR-16-2 | TTCCACTCTAGCAG CACGTAAA (SEQ ID No 5) | GTCACACTAAAGCA GCACAATAA (SEQ ID No 6) |
| Pre-miR-21 | GTACCACCTTGTCG GGTAGC (SEQ ID No 7) | CAAAATGTCAGACA GCCCATC (SEQ ID No 8) |
| Pre-miR-34c | GGCAGTGTAGTTAG CTGATTGCT (SEQ ID No 9) | TCTTTTTACCTGGC TGTGTGG (SEQ ID No 10) |
| B-actin* | AGCTGAGAGGGAAA TTGTGCG (SEQ ID No 11) | GCAACGGAACCGCT CATT (SEQ ID No 12) |

*B-actin primers from University of Kent.

Lipofectamine Transfection

For transient transfection experiments in 6 well plates the cell lines were seeded in the exponential growth phase at $3 \times 10^5$ cells·mL$^{-1}$ into 6-well plates (Greiner, U.K.) containing appropriate media and grown at 37° C. in a humidified 5% $CO_2$ in air (v/v) incubator. In 2 different tubes the following was prepared; (a) 4 µg of DNA and 250 µL of Gibco® OptiMEM medium (Life Technologies, UK), (b) 12 µL of Lipofectamine (Invitrogen, Life Technologies, UK) with 250 µL of Gibco® OptiMEM medium (Life Technologies, UK). These were then incubated at room temperature for 5 min, and the two tubes were mixed and incubated at room temperature for 20 min. At the end of this period, 500 µL of the DNA complex was added to the appropriate wells. The cells were cultured for different time periods before counting the cells and collecting a portion of the medium for mAb titre determination by ELISA.

For transient transfection experiments using various CHO-K1SV cell lines in 96-well deep well plates, the protocol for the 6 well plate transient transfection experiments was adjusted to take account of the larger number of cells. Cells were seeded in the exponential growth phase at $0.4 \times 10^6$ cells per well into 96-well deep well plates (Nunc) at 37° C. in a humidified 5% $CO_2$ in air (v/v) orbital shaking incubator at 375 rpm. 0.4 µg of DNA, 50 µL of Gibco® OptiMEM medium (Life Technologies, UK) and 1.2 µL of Lipofectamine (Invitrogen, Life Technologies, UK) were used per well, and prepared as above. Transfected cells were left for different time periods before counting the cells and collecting the medium in order to determine the mAb titre in the medium by ELISA.

ELISA

To determine mAb concentration, 100 µL of supernatant medium from transient transfections were analysed using a standard ELISA-based method (Smales et al. 2004 Biotechnology Bioengineering 88:474-488).

Statistical Analysis

To determine whether there were statistically significant differences in IVC, qP or the concentration of mAb in the supernatant medium between experimental conditions and controls, a student's t-test was undertaken. Changes were considered significant when a p value $P<0.05$ (at 95% confidence level) was obtained.

Example 1

Initial Identification of miR Targets Using the miRCURY LNA Microarray

The initial work to identify miRs whose expression may be associated with either qP or IVC was undertaken by using a commercially available miRCURY LNA microarray approach (Exiqon, Denmark). Two approaches were taken:

A) The first approach was to compare miR responses in a GS-CHOK1SV cell line (expressing a model recombinant chimeric mAb, cB72.3) grown in 10 L airlift bioreactors in batch and fed-batch mode. The fed-batch mode used Lonza's generic feeding regime (generic process—version 6). Three batch-mode bioreactors (n=3) were compared to three fed-batch mode reactors (n=3) for the GS-CHOK1SV 42 cell line (producing the chimeric mAb, cB72.3). Five points on each growth curve were selected for sampling (Table 2). For points 1-3, RNA samples were prepared from all six bioreactors (1=immediately pre-application of feed1 (pre-feed1), 2=48 h post-feed1 and 3=peak viable cell concentration). After peak, the unfed (batch-mode) bioreactors began to decline and no further sampling was taken from this set of bioreactors. Two further time points were taken from the three bioreactors receiving the feeds (fed-batch mode reactors, F17, F18 and F19) at 48 h post application of the second feed (4=48 h post-feed2) and at harvest (5=harvest). Thus, in total 24 samples were taken and RNA prepared from them using the miRNeasy kit (Qiagen) according to manufacturer's instructions. A 25th reference sample was prepared which consisted of a mixture of 5 µg of RNA from each of the 24 RNA preparations.

TABLE 2

Cell line '42' growth in 10 L airlift bioreactor culture.
Bioreactors were either run in batch or fed-batch mode.

| Elapsed time (day) | Sampling point | Bioreactors run in batch mode | | | Bioreactors run in fed-batch mode | | |
|---|---|---|---|---|---|---|---|
| | | F13 | F14 | F16 | F17 | F18 | F19 |
| | | Viable cell concentration ($10^6$ cells · mL$^{-1}$) | | | | | |
| 0 | | 0.2 | 0.2 | 0.2 | 0.2 | 0.2 | — |
| 1 | | 0.2 | 0.3 | 0.3 | 0.3 | 0.3 | 0.3 |
| 2 | | 0.7 | 0.6 | 0.7 | 0.5 | 0.6 | 0.4 |
| 3 | | 0.6 | 0.5 | 0.7 | 0.5 | 0.6 | 0.6 |
| 4 | | 1.7 | 1.7 | 1.9 | 1.7 | 1.7 | 1.8 |
| 5(f1) | 1 (pre-feed 1) | 1.9 | 3.0 | 3.0 | 3.1 | 3.0 | 2.7 |
| 6 | | 2.3 | 3.8 | 3.3 | 4.0 | 3.9 | 4.1 |
| 7 | 2 | 2.3 | 4.4 | 4.3 | 4.7 | 4.4 | 5.0 |
| 8 | | 2.5 | 4.8 | 4.8 | 6.0 | 5.8 | 6.3 |
| 9 | | 2.5 | 5.6 | 5.4 | 6.8 | 6.5 | 7.3 |
| 10(f2) | 3 | 2.3 | 5.5 | 4.9 | 6.8 | 6.7 | 7.2 |
| 11 | | 2.0 | 5.2 | 4.7 | 6.8 | 6.5 | 7.5 |
| 12 | 4 | 1.6 | 4.3 | 4.1 | 6.6 | 6.5 | 7.5 |
| 13 | | 1.5 | 3.8 | 3.0 | 7.4 | 6.6 | 7.7 |
| 14 | 5 | 1.3 | 2.7 | 2.1 | 7.3 | 6.5 | 7.4 |

Note:
for batch cultures no further sampling occurred after day 9 and for fed-batch cultures, f1 and f2 indicate application of the first and second feeds, respectively.

The samples were labelled with Hy3 and the reference with Hy5 and each sample hybridized against the reference on 24 miRCURY LNA (locked nucleic acid) microarrays. The data represented here are normalised log median ratios (ln(Hy3/Hy5)) values for miRs from comparing groups of reactors by ANOVA. Only those with $p<0.05$ (Table 3) were entered into the 2-way hierarchical clustering algorithm. From this analysis a number of interesting miR clusters (containing mmu-miR-21, -34b, -34c, -29a, -130a and -193) were identified that showed differences in expression between growth stages or between feeding processes. The miR identified in the array study may be involved in control of cell cycle and apoptosis. Large changes were observed in the amount of mmu-miR-34b and -34c. miRs mmu-miR-34a, -34b and -34c are all closely related and miR-34a is known to be a target for p53 leading to apoptosis and G1 arrest.

TABLE 3

Ranking of miRs by average fold-change between fed-batch day 12 and the reference. Significance testing was by ANOVA and the associated p-values are shown. MiRs listed in bold are of particular interest. The log median expression ratios for each miR were converted to fold changes using the following Microsoft Excel formula: "=POWER(2,A1)", where A1 is the cell containing the average of the log median normalised expression ratio (ln(Hy3/Hy5)).

| | Average fold-change | | |
|---|---|---|---|
| miR | Batch day 9 | Fed-batch day 12 | p-value |
| mmu-miR-34b | 2.28 | 4.09 | 1.41E-05 |
| mmu-miR-21 | 3.03 | 4.06 | 5.73E-10 |
| mmu-miR-34c | 2.22 | 4.03 | 4.25E-05 |
| mmu-miR-22 | 1.83 | 1.99 | 4.51E-03 |
| mmu-miR-130a | 1.73 | 1.94 | 1.33E-03 |
| mmu-miR-29a | 1.75 | 1.92 | 1.53E-06 |
| mmu-miR-23a | 2.13 | 1.76 | 2.41E-03 |
| mmu-miR-26b | 1.68 | 1.68 | 8.30E-05 |
| mmu-miR-26a | 1.90 | 1.63 | 8.55E-03 |
| mmu-miR-30b | 1.46 | 1.56 | 8.48E-06 |
| mmu-miR-193 | 1.26 | 1.54 | 1.59E-04 |
| mmu-miR-700 | 2.02 | 1.51 | 4.59E-04 |
| mmu-miR-23b | 1.50 | 1.43 | 6.90E-05 |
| mmu-let-7c | 1.18 | 1.36 | 2.45E-07 |
| mmu-miR-30c | 1.40 | 1.29 | 1.32E-04 |

TABLE 3-continued

Ranking of miRs by average fold-change between fed-batch day 12 and the reference. Significance testing was by ANOVA and the associated p-values are shown. MiRs listed in bold are of particular interest. The log median expression ratios for each miR were converted to fold changes using the following Microsoft Excel formula: "=POWER(2,A1)", where A1 is the cell containing the average of the log median normalised expression ratio (ln(Hy3/Hy5)).

| miR | Average fold-change | | p-value |
|---|---|---|---|
| | Batch day 9 | Fed-batch day 12 | |
| mmu-let-7b | 1.17 | 1.29 | 1.84E−05 |
| mmu-miR-29b | 1.20 | 1.26 | 5.03E−07 |
| hsa-miR-3180-3p | 1.16 | 1.22 | 1.24E−08 |
| mmu-let-7d* | 1.23 | 1.22 | 2.39E−03 |
| mmu-miR-31 | 1.53 | 1.18 | 9.83E−03 |
| mmu-miR-669c | 0.97 | 1.13 | 6.97E−03 |
| mmu-miR-669a | 1.10 | 1.09 | 4.10E−06 |
| hsa-miR-193a-5p | 1.14 | 1.09 | 1.47E−03 |
| mmu-miR-125a | 0.90 | 1.06 | 1.15E−06 |
| mmu-miR-185 | 1.08 | 1.05 | 2.85E−04 |
| mmu-miR-10a | 1.26 | 1.04 | 6.40E−03 |
| mmu-miR-710 | 0.93 | 0.99 | 2.49E−03 |
| hsa-miR483-5p | 1.01 | 0.99 | 1.85E−06 |
| hsa-miR-371a-5p | 1.04 | 0.96 | 5.96E−04 |
| mmu-miR-290 | 1.14 | 0.94 | 1.40E−04 |
| hsa-miR-483-5p | 0.92 | 0.93 | 2.76E−04 |
| mmu-miR-705 | 0.99 | 0.93 | 8.34E−07 |
| miRPlus__17836 (hsa-miR-30b-3p) | 0.94 | 0.92 | 2.04E−03 |
| hsa-miR-885-5p | 0.94 | 0.89 | 4.22E−04 |
| mmu-miR-129-5p | 1.02 | 0.87 | 7.28E−04 |
| mmu-miR-468 | 0.95 | 0.84 | 7.08E−08 |
| mmu-miR-452 | 0.86 | 0.84 | 1.96E−03 |
| mmu-miR-210 | 0.82 | 0.84 | 1.46E−04 |
| mmu-miR-292-5p | 0.99 | 0.83 | 2.67E−05 |
| mmu-miR-671 | 0.92 | 0.83 | 5.75E−04 |
| miRPlus__17861 | 0.94 | 0.78 | 8.09E−07 |
| mmu-miR-298 | 0.84 | 0.74 | 7.77E−07 |
| hsa-miR-491-3p | 0.75 | 0.72 | 1.07E−03 |
| hsa-miR-501-3p | 0.74 | 0.72 | 2.53E−04 |
| miRPlus__17832 | 0.76 | 0.71 | 5.52E−06 |
| mmu-miR-467a | 0.75 | 0.70 | 1.21E−05 |
| mmu-miR-714 | 0.76 | 0.68 | 4.00E−03 |
| mmu-miR-720 | 0.80 | 0.67 | 2.15E−04 |
| mmu-miR-706 | 0.83 | 0.65 | 6.31E−09 |
| mmu-miR-709 | 0.65 | 0.63 | 8.27E−04 |
| mmu-miR-467b | 0.67 | 0.56 | 3.97E−05 |
| hsa/bta-miR-21-3p | 0.68 | 0.54 | 4.69E−06 |
| mmu-miR-691 | 0.62 | 0.50 | 4.47E−05 |
| hsa-miR-665 | 0.62 | 0.48 | 2.63E−05 |
| hsa-miR-185-3p | 0.62 | 0.47 | 3.98E−08 |

B) The second approach was to profile miRs across a panel of 10 GS-CHOK1SV cell lines with different cB72.3 mAb productivities. This was undertaken by analysing cell samples taken from triplicate batch shake-flask cultures of 10 GS-CHO cell lines with a range of productivities for cB72.3 mAb in batch suspension culture (Table 4).

TABLE 4

Concentration of mAb at harvest in batch suspension culture of the 10 recombinant GS-CHOK1SV cell lines expressing the cB72.3 antibody. Values are the mean (±SD) of three cultures, with the exception of cell line 56 which is the mean two cultures.

| Cell Line | [mAb] at harvest (mg/L) |
|---|---|
| 153 | 11 ± 0 |
| 1 | 223 ± 5 |
| 142 | 254 ± 43 |
| 54 | 303 ± 5 |
| 114 | 313 ± 64 |
| 40 | 349 ± 2 |
| 56 | 414 ± 11 |
| 137 | 472 ± 14 |
| 149 | 524 ± 13 |
| 42 | 550 ± 4 |
| 47 | 644 ± 14 |

RNA was extracted from the cell pellets collected during the exponential growth phase and subjected to analysis on the miRCURY LNA microarray (Exiqon, Denmark). Cell lines were ranked and separated into two equally-sized groups, based on the cB72.3 concentration from batch suspension cultures (Table 4: 'low' producer cell lines: 153, 1, 142, 54, 114; 'high' producer cell lines: 40, 137, 149, 42, 47). Normalised log median expression ratios (ln(Hy3/Hy5)) for each miR were then analysed to identify relationships with productivity. The miR profiling identified a subset (15) of the total number of miRs analysed by the miR-CURY™ microarray that are differentially expressed in the high and low producer groups using mouse annotation and 18 miRs using human annotation. Heat map diagrams for the human and mouse annotations were prepared. The p values from ANOVA from the human and mouse annotation results are reported in Tables 5 and 6.

TABLE 5

ANOVA calculated p-values between miRs differentially regulated between 'high' and 'low' producer groups. Analysis was performed using the miRCURY LNA microarray between 'high' and 'low' producer groups for mouse annotations. MiRs of particular interest are highlighted in bold.

| Probe Set | p-value |
|---|---|
| mmu-let-7b | 3.51E−03 |
| mmu-let-7d | 7.68E−03 |
| mmu-let-7f | 5.80E−03 |
| mmu-miR-137 | 1.71E−05 |
| mmu-miR-146a | 2.05E−03 |
| mmu-miR-15b | 3.09E−04 |
| mmu-miR-16 | 3.24E−04 |
| mmu-miR-186 | 8.43E−03 |
| mmu-miR-18a | 8.06E−03 |
| mmu-miR-19a | 1.89E−04 |
| mmu-miR-19b | 1.47E−03 |
| mmu-miR-382 | 1.38E−04 |
| mmu-miR-483 | 3.23E−03 |
| mmu-miR-711 | 3.54E−03 |
| mmu-miR-882 | 9.89E−08 |

TABLE 6

ANOVA calculated p-values between miRs differentially regulated between 'high' and 'low' producer groups. Analysis was performed using the miRCURY LNA microarray between 'high' and 'low' producer groups for human annotations. MiRs of particular interest are highlighted in bold.

| Probe Set | p-value |
|---|---|
| hsa-let-7b | 3.51E−03 |
| hsa-let-7d | 7.68E−03 |
| hsa-let-7f-1 | 5.80E−03 |
| hsa-miR-137 | 1.71E−05 |
| hsa-miR-146a | 2.05E−03 |
| hsa-miR-15b | 3.09E−04 |

TABLE 6-continued

ANOVA calculated p-values between miRs differentially regulated between 'high' and 'low' producer groups. Analysis was performed using the miRCURY LNA microarray between 'high' and 'low' producer groups for human annotations. MiRs of particular interest are highlighted in bold.

| Probe Set | p-value |
| --- | --- |
| hsa-miR-16 | 3.24E−04 |
| hsa-miR-186 | 8.43E−03 |
| hsa-miR-18a | 8.06E−03 |
| hsa-miR-19a | 1.89E−04 |
| hsa-miR-19b | 1.47E−03 |
| hsa-miR-382 | 1.38E−04 |
| hsa-miR-576-3p | 1.96E−03 |
| hsa-miR-583 | 9.44E−06 |
| hsa-miR-605 | 4.33E−03 |
| hsa-miR-617 | 6.49E−03 |
| hsa-miR-620 | 4.17E−03 |
| miRPlus__17891 | 5.12E−04 |

From these initial microarray studies five miRs were identified that showed increased expression related to growth (miR-21, miR-34c) or productivity (miR-15b, miR-16 and miR-186).

Example 2

Validating Endogenous miR Expression Levels Throughout Batch Culture and in 'High' and 'Low' Producer Recombinant mAb-Producing GS-CHOK1SV Cell Lines Having identified a number of miRs using the miRCURY LNA microarray system whose expression might be associated with either IVC or qP as described in Example 1, four target miRs, namely miR-15b, miR-16, miR-21 and miR-34c, were further analysed with respect to their influence on recombinant protein expression in GS-CHOK1SV cell lines.

Before manipulating the levels of the miRs by transient transfection (Example 3 to 5, using an approach similar to that outlined by Jadhav et al. (2012 Biotechnology and Bioengineering 109:1376-1385). It was first necessary to show that the microarray results were consistent with measurements of the target miRs in recombinant GS-CHOK1SV cell lines by qRT-PCR. To achieve this three cell lines were selected (Example 1 b) for further analysis differing in productivity (Table 4) and IVC (see FIG. 1). Samples were taken (a set number of cells at each point) throughout culture at the points indicated by arrows for analysis of the miR amounts etc.

After miR extraction was completed using the MirVANA RNA Extraction Kit, miR amounts were determined using the commercially available two-step TaqMan® MicroRNA Assay kit (Applied Biosystems). In order to determine the concentrations of mature miRs in each sample a standard curve was prepared for each miR.

Using this qRT-PCR the concentrations of the four target miRs in GS-CHOK1SV cell lines were determined across batch culture in the Lonza cB72.3 producing GS-CHOK1SV cell lines: GS-CHO 42 (high' producer) and GS-CHO 114 ('low' producer). The data obtained was compatible with the microarray data. The data in FIGS. 2 to 5 shows (A) the amount of the immature pre-miR normalised to β-actin and relative to the first day samples collected and (B) the concentration of mature miR determined from the standard curves at the various time points.

The concentration of miR-15b in the two test cell lines throughout batch culture is reported in FIG. 2. Although the pre-miR amounts in both cell lines showed similar profiles throughout culture (FIG. 2A), the amount of pre-miR-15b in the 120 h and 168 h samples was greater for the 'high' producer cell line. As can be seen from the data, the trend in the amounts of the mature miR is different between the two cell lines, decreasing throughout culture in the 'low' producer and only appearing at the end of culture in the 'high' producer (FIG. 2B). Thus there was no relationship between the pre-miR-15b and mature miR-15b amounts. This data concurred with the microarray data in which miR-15b levels were elevated in some 'high' producer cell lines at day 4 of batch culture.

The relative amount of pre-miR-16 and concentration of miR-16 in the 'high' and 'low' producer cell lines throughout batch culture is reported in FIG. 3. In the 'high' producer there is 40-50% more pre-miR-16-1 present than the 'low' producer throughout culture (FIG. 3A). The relative amount of pre-miR-16 for both cell lines peaks at 168 h (for pre-miR-16-1) and 120 h (for pre-miR-16-2) (FIGS. 3A and 3B, respectively) and their profiles were similar to those observed for pre-miR-15b (FIG. 2A). However, once again the profile of the mature miR-16 was different. The concentration of mature miR decreased across culture in both cell lines, although the concentration was always higher in the 'high' producer cell line (FIG. 3C). This is consistent with the microarray data showing that miR-16 is elevated in some 'high' producer cell lines at day 4 of culture.

The relative amount of pre-miR-21 and concentration of miR-21 in the higher and lower-producer cell lines throughout batch culture is reported in FIG. 4. Between 72 and 120 h of culture time, pre-miR-21 showed a large increase in the 'low' producer cell line, whilst the 'high' producer cell line had lower relative amounts of pre-miR-21 that only increased between 120 h and 168 h of culture (FIG. 4A). The concentration of miR-21 in the 'low' producer cell line increases up to 168 h of culture time then drops between 168 h and 264 h of culture time, whilst in the 'high' producer cell line the concentration of miR-21 continues to increase throughout culture (FIG. 4B).

The relative amount of pre-miR-34c and concentration of miR-34c in the 'high' and 'low' producer cell lines throughout batch culture is reported in FIG. 5. A different trend was observed between the 'high' and 'low' producer cell lines with respect to pre-miR34-c and mature miR-34c (FIG. 5). Although the relative amount of pre-miR-34c in both cell lines showed similar profiles throughout culture (FIG. 5A), the relative amount of pre-miR-34c in the 120 h and 168 h samples was higher for the 'high' producer cell line. For both cell lines, it was observed that the profile of relative amounts of pre-miR-34c reflects that of the concentration of mature miR-34c. In the 'high' producer cell line, the amount of pre-miR-34c appeared to increase throughout culture, much less so in the case of the 'low' producer cell line (FIG. 5A). The concentration of miR-34c in the 'high' producer cell line increases between 72 h and 168 h of culture time, but falls again at 264 h (FIG. 5B). However, in the 'low' producer cell line the concentration of miR-34c falls by 168 h of culture (FIG. 5B).

The qRT-PCR data for the mature miRs was therefore generally consistent with the microarray data as described above.

Examples 3 to 5 show the transient over-expression of the mature miRs and demonstrates that over-expression can modify the phenotype of the GS-CHOK1SV cell lines investigated, e.g. specific production rate, qP or the integral of viable cell concentration, IVC. In these examples, the transient over-expression of both individual and combinations of miRs was analysed using a plasmid based-approach as described in the following sections.

Example 3

Investigating the Effect of the Over-Expression of Exogenous miR Expression Levels on Productivity in Recombinant GS-CHOK1SV Cell Lines Expressing a Model mAb (cB72.3)

To confirm functional effects of the miRs investigated, transient studies were undertaken. Vectors that express the stem-loops of human pre-miRs flanked by the appropriate pre-miR genomic sequence were generated and used for transient expression. The expected sequence was confirmed by restriction enzyme digestion and sequencing. Transient expression of miRs in CHO cells is reported to be higher when using the CHO-derived stem-loops, although other species can also be used to over-express pre-miRs. However, a lower amount of over-expression may be beneficial as too high an elevation in the concentration of exogenous miR could be detrimental.

To confirm the functionality of these plasmids, CHOK1SV cells were transiently transfected with an expression vector encoding pre-miR21. RNA extracts from control cells (transfected with a blank plasmid) and pre-miR-21-transfected cells were analysed by northern blotting. The amount of mature miR-21 was elevated in CHOK1SV cells transiently transfected with the pre-miR-21 construct (data not shown). Relatively large amounts of pre-miR were observed in all samples compared to mature levels. This data shows the vectors are functional and can be used in for over-expression or 'knock-up' studies.

Example 4

Transient Transfection and Over-Expression of Target miRs in 6-Well Plates

Four vectors expressing the stem-loops of human pre-miR miR-15b, -16, -21 and -34c were constructed. These vectors were used to investigate the effect of exogenous miRs on the qP and IVC in the 'low' and 'high' producer cell lines used in the validation of the microarray data (Example 4). In the first set of experiments, cells were grown and transfected with the over-expression vectors in a 6-well plate format in static mode incubators. The effect of each vector on qP and IVC determined post-transfection are presented in FIG. 6. In this cell culture format, miR-15 was the only exogenously expressed miR to increase IVC by 50% (compared to transfectant blank) and then only in the 'high' producer cell line (FIG. 6A). In terms of qP, only exogenously expressed miR-34c engendered a significant increase (compared to transfectant blank) and this occurred both in the 'low' and 'high' producer cell lines (FIG. 6B). This suggests that miR-34c may target processes involved in determining qP that are common to both 'high and 'low' producing cell lines.

The effect of these miRs was further analysed by transiently expressing the over-expression vectors into the same two mAb-producing GS-CHOK1SV cell lines, this time grown in suspension culture in 96-well deep well shaken plates. As all the GS-CHOK1SV cell lines described in this patent grow in suspension culture, this mode of culture is more appropriate to these cell lines and is closer to the manufacturing process.

Example 5

Transient Transfection and Over-Expression of Target miRs in Shaking 96-Well Deep Well Plates In order to assess the influence of miR over-expression, and combinations of miR over-expression in an environment that can approximate better to the environment found in a bioreactor, experiments were undertaken in shaken 96-well deep well plates. GS-CHOK1SV cell lines producing cB72.3 mAb were transiently transfected in suspension separately with a single vector encoding one miR or in co-transfections where two or three miR-encoding vectors were combined. For the single transfections, cells and culture medium were sampled at 48 h post-transfection, whilst co-transfections were sampled at either 48 h or 96 h post-transfection. For each transfection, growth (IVC) and product titre (determined by ELISA) were determined. Three different cB72.3-producing GS-CHOK1SV cell lines were used to determine if any observed effects were cell line-specific: 'High' and 'low' producing lines CHO 42 and CHO 114, respectively, plus CHO-56 which was deemed a 'mid' producer cell line.

(i) CHO 42 ('High' mAb Producer)

CHO 42 cells transiently co-transfected with separate vectors either encoding pre-miR-34c and pre-miR-15b, pre-miR-15b and pre-miR16 or pre-miR-16 and pre-miR-34c all showed a statistically significant increases (20.77%, 33.24% and 38.7%, respectively) in the concentration mAb in the culture medium 96 h post-transfection (FIG. 7).

(ii) CHO 56 ('Mid' mAb Producer)

CHO 56 cells transiently co-transfected with separate vectors encoding pre-miR-15b and pre-miR-16, pre-miR-16 and pre-miR-34c or pre-miR-15b with pre-miR-16 and pre-miR-34c showed statistically significant increases (58.7%, 57.8% and 71.1%, respectively) in the concentration of mAb in the culture medium after 96 h post-transfection (FIG. 8).

(iii) CHO 114 ('Low' mAb Producer)

In the case of the CHO 114 cell line, only those transfected with the vector encoding pre-miR-34 showed a statistically significant increase in the concentration of mAb in the culture medium 48 h after transfection (FIG. 9A). However, by 96 h post-transfection all the co-transfection combinations showed statistically significant increases in the concentration of mAb secreted into the culture medium to varying degrees (FIG. 9B).

The combined data from transient studies in the different cell lines shows that either individual over-expression of pre-miR-15b, pre-miR-16 or pre-miR-34c, or combinations of these, can influence recombinant mAb expression in one or more cell lines producing the same mAb with different productivities.

To further investigate this transfectant pools were generated from the CHOK1SV host engineered to stably over-express the individual pre-miRs.

Example 6

Generation of CHOK1SV Host Pools Engineered to Stably Over-Express Individual miRs Transfectant pools over-expressing the individual pre-miRs were created in CHOK1SV host cells (Lonza Biologics). To achieve this, the aforementioned vectors encoding various pre-miRs were used which additionally contain a puromycin selection marker. These vectors were transfected by electroporation into the Lonza CHOK1SV host cell line followed by selection in puromycin-containing medium.

Puromycin-resistant pools were analysed for growth (FIG. 10) and miR content (FIG. 11) to confirm that the amount of specific mature miR (i.e., the one encoded in pre-miR form by the transfected vector and processed to the mature miR form by the cell) was elevated in the pools. During batch culture there was no significant difference in growth characteristics of the pools compared to the control pool (i.e., CHOK1SV separately transfected with an identical vector containing a puromycin marker without encoding a pre-miR). However, the concentrations of specific miR (related to the pre-miR-encoding vector used to create the pool) in each pool was increased by 2- to 3-fold in all the pools compared to the control pool and the original CHOK1SV host (FIG. 11).

In order to test the performance of the pool expressing exogenous miR-34c, it was transiently super-transfected with a luciferase reporter gene with or without a sponge sequence (i.e. a complementary or near complementary miR target sequence; Ebert M. S. et al. 2007 Nature Methods 4:721-726) in the 3'-UTR (FIG. 12). As the miR-34c levels appear to be elevated in the pool, this should result in lower reporter activity than in the control. The stable pool was also transiently super-transfected with the same vector (used to create the pool) encoding miR-34c to determine if this has any further effect on reporter gene activity. As shown in FIG. 12, when the luciferase reporter was transfected into the miR-34c-expressing pool, the presence of the miR-34c sequence resulted in a decrease in luciferase expression of approximately 65%, consistent with the processing of over-expressed pre-miR-34c into mature miR-34c. When additional pre-miR-34c-encoding vector was transfected into the pool a further reduction in luciferase reporter expression was only observed if the target sequence was present in the luciferase reporter transcription cassette (FIG. 12). The reporter activity was only elevated in the pre-miR-34c stable pool compared to the control cell line. This observation is in agreement with the results observed upon transient over-expression of miR-34c in the mAb-producing cell lines, where an increase in the concentration of mAb in the medium was observed. These results show that pre-miR-34c over-expression leads to enhanced transgene expression (via successful cell-processing of the exogenous pre-miR-34c to mature miR-34c), and that CHOK1SV cells are competent to process pre-miR-34c into functional mature miR-34c (as determined by a qRT-PCR assay specific for mature miR).

The invention claimed is:

1. A method for the preparation of a protein production engineered mammalian producer cell capable of increasing production of a protein of interest, the method comprising:
   a) providing a mammalian producer cell;
   b) increasing the concentration of a combination of miRs selected from the group consisting of miR-15 and miR-34; miR-16 and miR-34; and miR-15, miR-16, and miR-34 in the mammalian producer cell by transfecting the mammalian producer cell with:
      (i) the combination of miRs,
      (ii) at least one vector containing a nucleotide sequence encoding the combination of miRs under control of at least one regulatory element allowing overexpression of the miRs, or
      (iii) with two or more vectors containing nucleotide sequences encoding individual miRs of the combination of miRs under control of at least one regulatory element allowing overexpression of the combination of miRs,
   so as to obtain a protein production engineered mammalian producer cell; and
   c) recovering the protein production engineered mammalian producer cell produced in step b), wherein the mammalian producer cell is a CHO cell, a CHO-K1 cell or a CHO-K1 SV cell; and
   wherein increasing the concentration of the combination of miRs in accordance with step (b) increases production of the protein of interest in comparison with cells in which the combination of miRs are not increased.

2. The method according to claim 1, wherein the miR-15 is miR-15a or miR-15b.

3. The method according to claim 1, wherein the miR-34 is miR-34a, miR-34b or miR-34c.

4. The method according to claim 1, wherein the combination of miRs comprises mature miRs, precursor miRs, or primary miRs.

5. The method according to claim 1, wherein the at least one vector encoding the combination of miRs in step b) is transiently or stably transfected.

6. The method according to claim 1, wherein the mammalian producer cell is transfected with a nucleotide sequence encoding the protein of interest prior to step a) or during step b).

7. The method according to claim 1, wherein the protein production engineered mammalian producer cell obtained after step b) is transfected with a nucleotide sequence encoding the protein of interest.

8. The method according to claim 1, wherein the regulatory element allowing the overexpression of the combination of miRs is a promoter.

9. The method according to claim 1, wherein the protein production engineered mammalian producer cell is a cell exhibiting an increased specific production rate or an increased time integral of viable cell concentration or both.

10. A protein production engineered mammalian producer cell produced according to the method of claim 1.

11. The method according to claim 1, wherein the mammalian producer cell comprises an exogenous nucleotide sequence that expresses the protein of interest and wherein the transfecting the mammalian producer cell with the combination of miRs comprises transfecting the mammalian producer cell with nucleotide sequences encoding for stem loops of human pre-miR-15 and pre-miR-34; stem loops of human pre-miR-16 and pre-miR-34; or stem loops of human pre-miR-15, pre-miR-16, and pre-miR-34.

12. The method according to claim 1, wherein the protein of interest is a chimeric antibody, a heavy chain of an antibody, a light chain of an antibody, a variable region of an antibody, or a constant region of an antibody.

13. The method according to claim 1, wherein the protein of interest is follicle-stimulating hormone (FSH), factor VIII, thrombopoietin (TPO), erythropoietin (EPO), G-CSF, GM-CSF, tissue-plasminogen activator (TPA), interferon a, interferon 13, interferon y, insulin-like growth factor, or somatotropin.

14. The method according to claim 1, further comprising;
   d) cultivating the protein production engineered mammalian producer cell; and
   e) recovering the protein of interest from the protein production engineered mammalian producer cell.

* * * * *